(12) United States Patent
Haynes et al.

(10) Patent No.: US 7,153,509 B2
(45) Date of Patent: Dec. 26, 2006

(54) IMMUNOGENIC PEPTIDES COMPRISING A T-HELPER EPITOPE AND A B-CELL NEUTRALIZING ANTIBODY EPITOPE

(75) Inventors: Barton F. Haynes, Durham, NC (US); Bette T. Korber, Los Alamos, NM (US); Robert M. De Lorimier, Durham, NC (US)

(73) Assignees: Duke University, Durham, NC (US); The Regents of the University of Calforinia, Oakland, CA (US)

( * ) Notice: Subject to any disclaimer, the term of this patent is extended or adjusted under 35 U.S.C. 154(b) by 0 days.

(21) Appl. No.: 10/289,228

(22) Filed: Nov. 7, 2002

(65) Prior Publication Data

US 2003/0147888 A1 Aug. 7, 2003

Related U.S. Application Data

(60) Provisional application No. 60/331,036, filed on Nov. 7, 2001.

(51) Int. Cl.
*A61K 39/00* (2006.01)

(52) U.S. Cl. .................. 424/192.1; 424/188.1; 424/202.1; 424/204.1; 424/208.1; 424/278.1; 530/324; 530/826

(58) Field of Classification Search ............ 530/324, 530/826; 424/192.1, 188.1, 202.1, 204.1, 424/208.1, 278.1
See application file for complete search history.

(56) References Cited

U.S. PATENT DOCUMENTS

| | | | |
|---|---|---|---|
| 5,013,548 | A | 5/1991 | Haynes et al. |
| 5,019,387 | A | 5/1991 | Haynes et al. |
| 5,352,576 | A | 10/1994 | Haynes et al. |
| 5,516,632 | A | 5/1996 | Palker et al. |
| 5,643,756 | A | 7/1997 | Kayman et al. |
| 5,800,822 | A | 9/1998 | Sia et al. |
| 5,993,819 | A | 11/1999 | Haynes et al. |
| 6,114,143 | A | 9/2000 | Eda et al. |
| 2001/0003646 | A1 | 6/2001 | Haynes et al. |
| 2001/0036461 | A1 | 11/2001 | Haynes et al. |
| 2002/0086283 | A1 | 7/2002 | Haynes et al. |
| 2003/0147888 | A1 | 8/2003 | Haynes et al. |
| 2004/0001851 | A1 | 1/2004 | Haynes et al. |
| 2004/0039172 | A1 | 2/2004 | Haynes et al. |
| 2004/0086506 | A1 | 5/2004 | Haynes et al. |
| 2004/0132010 | A1 | 7/2004 | Haynes et al. |
| 2004/0197344 | A1 | 10/2004 | Haynes et al. |

FOREIGN PATENT DOCUMENTS

| | | |
|---|---|---|
| WO | WO 93/15750 | 8/1993 |
| WO | WO 95/29700 | 11/1995 |
| WO | WO 97/14436 | 4/1997 |
| WO | WO 01/56355 | 8/2001 |
| WO | WO 02/24149 | 3/2002 |
| WO | WO 03/039470 | 5/2003 |
| WO | WO 03/046137 | 6/2003 |
| WO | WO 2004/009785 | 1/2004 |
| WO | WO 2004/075850 | 9/2004 |
| WO | WO 2005/016952 | 2/2005 |

OTHER PUBLICATIONS

Pang et al. "HIV–1 env sequence variation in brain tissue of patients with AIDS–related neurologic disease", J. Acquir. Immune Defic. Syndr., vol. 4, No. 11 (1991), pp. 1082–1092.*

Haynes et al, HIV Vaccine Development at Duke University Medical Center, Immunologic Research 22(2–3):263–269 (2000).

Bartlett et al, "Safety and immunogenicity of an HLA–based HIV envelope polyvalent synthetic peptide immunogen", AIDS 12(11):1291–1300 (1998).

De Berardinis et al, "Phage display of peptide epitopes from HIV–1 elicits strong cytolytic responses", Nature Biotechnology 18:873–876 (2000).

U.S. Provisional Appl. No. 60/503,460 filed Sep. 17, 2003 and U.S. Provisional Appl. No. 60/604,722 filed Aug. 27, 2004 (see attached copy of PCT/US04/30397 filed Sep. 17, 2004).

U.S. Appl. No. 10/518,523 filed Dec. 21, 2004 (U.S. National Phase of WO 2004/009785 see above).

U.S. Appl. No. 10/973,977 filed Oct. 27, 2004.

U.S. Appl. No. 10/973,475 filed Oct. 27, 2004.

U.S. Provisional Appl. No. 60/625,720 filed Nov. 8, 2004.

Haynes et al, "HIV type 1 V3 region primer–Induced antibody suppresion is overcome by administration of C4–V3 peptides as a polyvalent immunogen", AIDS Research and Human Retrovirises 11(2):211–221 (1995).

Spicer et al, "Modification of anti–HIV antibody response and peptide solution conformations by point substitutions in chimeric gp120 C4–V3 immunogenic peptides", Abstrates of Papers America Chemical Society 218(1–2):MEDI 286 (1999) –XP009052973.

* cited by examiner

*Primary Examiner*—Jeffrey Stucker
(74) *Attorney, Agent, or Firm*—Nixon & Vanderhye P.C.

(57) ABSTRACT

The present invention relates, generally, to a polyvalent immunogen and, more particularly, to a method of inducing neutralizing antibodies against HIV and to a polyvalent immunogen suitable for use in such a method.

16 Claims, 4 Drawing Sheets

Lymphocytes

Monocytes

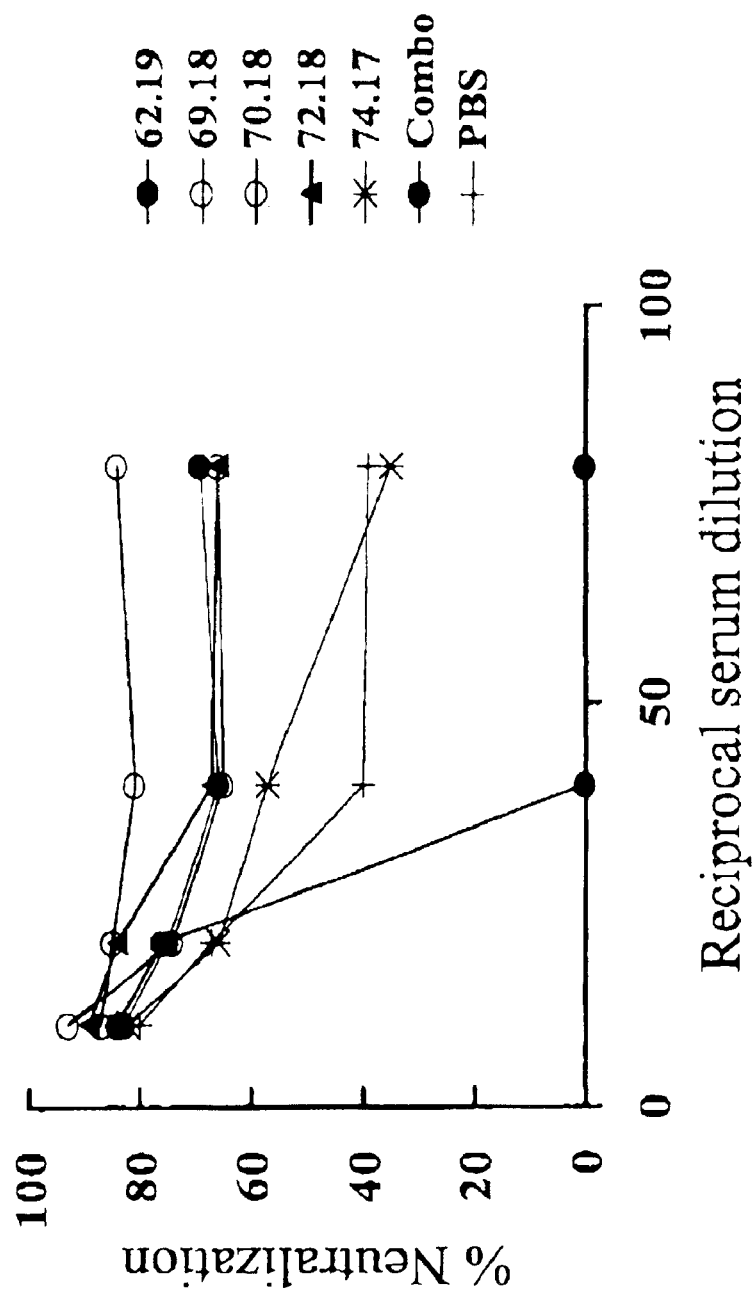

IMMUNOGENIC PEPTIDES COMPRISING A T-HELPER EPITOPE AND A B-CELL NEUTRALIZING ANTIBODY EPITOPE

This application claims priority from Provisional Application No. 60/331,036, filed Nov. 7, 2001, the content of which is incorporated herein by reference.

TECHNICAL FIELD

The present invention relates, generally, to a polyvalent immunogen and, more particularly, to a method of inducing neutralizing antibodies against HIV and to a polyvalent immunogen suitable for use in such a method.

BACKGROUND

Immunogenic peptides have been developed that elicit B and T cell responses to various strains of human immunodeficiency virus (HIV) (Palker et al, J. Immunol. 142:3612–3619 (1989), Haynes et al, Trans. Am. Assoc. Physician 106:31–41 (1993), Haynes et al, J. Immunol. 151:1646–1653 (1993), Haynes et al, AID Res. Human Retroviruses 11:211–221 (1995)) (see also WO 97/14436). These peptides consist of two components, each derived from noncontiguous regions of the HIV gp120 envelope protein. One envelope component consists of 16 amino acid residues from the fourth constant (C4) domain of HIV gp120, and includes a T-helper epitope (Cease et al, Proc. Natl. Acad. Sci. USA 84:4249–4253 (1987)). Linked to the carboxyl terminus of this gp120 C4 region peptide is a 23 amino acid segment from the third variable (V3) domain of gp120, that includes a B cell neutralizing antibody epitope for cell line-adapted HIV strains (Palker et al, J. Inmunol. 142:3612–3619 (1989), (Palker et al, Proc. Natl. Acad. Sci. USA 85:1932–1936 (1988), Rusche et al, Proc. Natl. Acad. Sci. USA 85:3198–3202)), a T-helper epitope (Palker et al, J. Immunol. 142:3612–3619 (1989)), and two cytotoxic T lymphopoietic (CTL) epitopes (Clerici et al, J. Immunol. 146:2214–2219 (1991), Safrit et al, 6$^{th}$ NCVDG Meeting, October 30 to Nov. 4, 1993)). In mice and rhesus monkeys, these C4-V3 hybrid peptides have induced antibodies that bind to native gp120 and neutralize the particular cell line-adapted strain of HIV from which the V3 segment was derived, as well as induce T helper cell proliferative responses and MHC Class I-restricted CTL responses that kill HIV or HIV protein expressing target cells (Palker et al, J. Immunol. 142:3612–3619(1989), Haynes et al, AID Res. Human Retroviruses 11:211–221 (1995)). Recently, it was shown that this gp120 peptide design can induce antibodies that neutralize primary HIV isolates and simian-human immunodeficiency viruses (SHIV) expressing primary HIV isolate envelopes (Liao et al, J. Virol. 74:254–263 (2000)). Moreover, in a challenge trial of this immunogen in rhesus monkeys, it was shown that C4-V3 peptides from the gp120 of the pathogenic SHIV 89.6P, induced neutralizing antibodies that prevented the fall in CD4 counts after challenge with SHIV 89.6P (Letvin et al, J. Virol. 75:4165–4175 (2001)). Therefore, anti-V3 antibodies can protect primates against primary isolate SHIV-induced disease.

A prototype polyvalent HIV experimental immunogen comprised of the conserved C4 region of gp120 and the V3 regions of HIV isolates MN, CANO(A), EV91 and RF has been constructed and has been found to be highly immunogenic in human clinical trials (Bartlett et al, AIDS 12:1291–1300 (1998), Graham et al, Abstract, AIDS Vaccine (2001)). Thus, understanding secondary and higher order structures of the components of this polyvalent immunogen, as well as defining strategies to optimize gp120 immunogen antigenicity, is important to HIV vaccine design efforts. In addition, recent data suggest that the HIV V3 region may be involved in regulating gp120 interactions with HIV co-receptors, CXC chemokine receptor 4 (CXCR4) and 13 chemokine receptor type 5 (CCR5) (Berger, AIDS Suppl. A:53–56 (1997)).

In previous studies, nuclear magnetic resonance (NMR) has been used to characterize conformations of the multivalent immunogen C4-V3 peptides in solution (de Lorimier et al, Biochemistry 33:2055–2062 (1994), Vu et al, Biochemistry 35:5158–5165 (1996), Vu et al, J. Virol. 73:746–750 (1999)). It as been found that the V3 segments of each of the four C4-V3 peptides displayed evidence of preferred solution conformations, with some features shared, and other features differing among the four peptides. The C4 segment, which is of identical sequence in all the peptides, showed in each case a tendency to adopt nascent helical conformations (de Lorimier et al, Biochemistry 33:2055–2062 (1994), Vu et al, Biochemistry 35:5158–5165 (1996), Vu et al, J. Virol. 73:746–750 (1999)).

The C4 domain of gp120 is part of the CD4 binding site, and antibodies recognizing the C4 sequence, block the binding of CD4 of gp120. However the C4 sequence as a peptide does not elicit antibodies that bind native gp120 (Palker et al, J. Immunol. 142:3612–3619 (1989), Haynes et al, J. Immunol. 151:1646–1653 (1993), Ho et al, J. Virol. 61:2024–2028 (1987), Robey et al, J. Biol. Chem. 270:23918–23921 (1995)). This led to the speculation that the nascent helical conformations exhibited by the C4 segment might reflect a conformation not native to HIV gp120. Amino-acid sequence homology between the gp120 C4 region and a human IgA CH1 domain has been noted (Maddon et al, Cell 47:333–348 (1986)). By comparison to the structure of mouse IgA (Segal et al, Proc. Natl. Acad. Sci. USA 71:4298–4302 (1974)), the C4-homologous region of IgA has a β strand secondary structure (de Lorimier et al, Biochemistry 33:2055–2062 (1994)). Therefore, while the C4 gp120 peptide in solution adopts nascent helical conformations, the native structure of this gp120 C4 region may be quite different (ie, in the context of gp 120 have a β strand secondary structure).

The present invention results, at least in part, from the results of a study with a three-fold purpose. First, C4-V3HIVRF peptides with amino acid substitutions designed to minimize C4 α-helical peptide conformation and promote β strand C4 secondary structures were constructed in order to induce anti-native gp120 antibodies with the modified C4 peptide. Second, tests were made to determine if any of these mutated C4-V3RF peptides would enhance gp120 V3 region peptide immunogenicity, and therefore augment anti-HI VRF gp120 V3 loop antibody responses. Finally, the solution conformers of each peptide studied immunologically were also solved using NMR to correlate peptide conformers with peptide immunogenicity.

SUMMARY OF THE INVENTION

The present invention relates to a method of inducing neutralizing antibodies against HIV and to peptides, and DNA sequences encoding same, that are suitable for use in such a method.

Objects and advantages of the present invention will be clear from the description that follows.

BRIEF DESCRIPTION OF THE DRAWINGS

FIG. 4: Neutralization of BAL in PBMC.

DETAILED DESCRIPTION OF THE INVENTION

Figure 1:
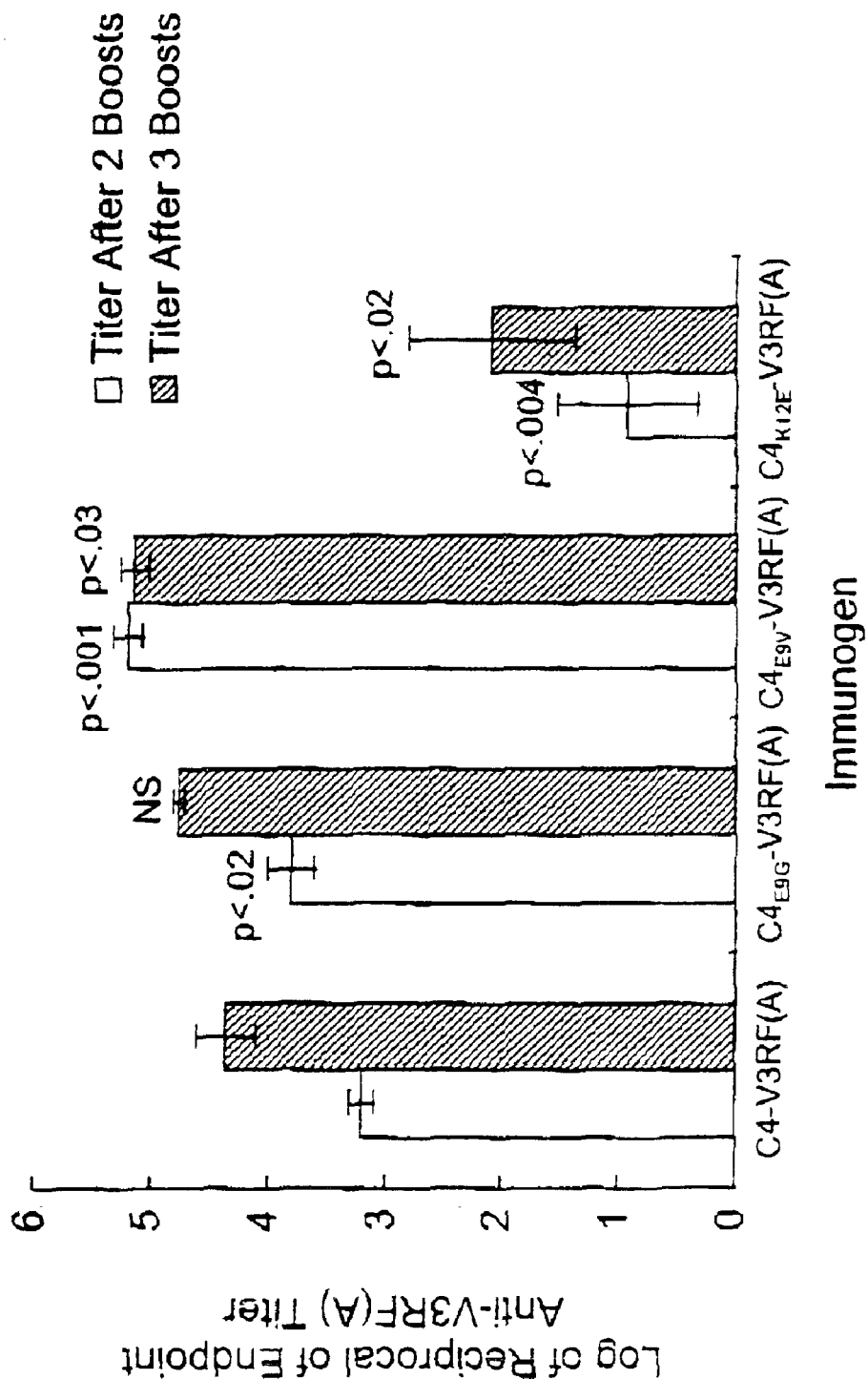
FIG. 1: Summary of antibody binding titers to immunizing peptide after 2 or 3 boosts of 3 mice in each group with immunizing peptide. There was a slight enhancement of levels of antibody induced by the E9G variant after 2 but not 3 boosts, while the E9V variant significantly boosted antibody levels compared to the C4-V3RF(A) peptide after 2 and 3 boosts. Antibody to the K12E variant induced by the K12E peptide was significantly lower than C4-V3RF(A) induced antibody levels after both 2 and 3 boosts.

The present invention relates to a composition comprising a multiplicity of immunogenic hybrid peptides, each comprising two components. One component includes a T-helper epitope and can comprise residues from the C4 domain of HIV gp120. The second component comprises residues from the V3 domain of gp120 and includes a B cell neutralizing antibody epitope.

Advantageously, the first component comprises about 16 contiguous residues from the C4 domain (about residues 421 to 436) and the second component comprises about 23–25 contiguous residues from the V3 domain (about residues 297 to 322). The components can, however, be longer or shorter. Preferably, the V3 component is linked C terminal to the C4 component peptide. The hybrid peptides can include additional sequences (e.g., linkers (e.g., cysteine, serine or lysine linkers) between the C4 and V3 components). The composition can, for example, comprise 5 to 10 hybrid peptides, 10 to 15 hybrid peptides or 25 to 30 hybrid peptides. The number of hybrid peptides used will depend, at least in part, on the target population.

Preferred first components comprising residues from the C4 domain are shown in the Tables that follow (see particularly Tables 6 and 7). Other T helper determinants from HIV or from non-HIV proteins can also be used. For example, a further T helper epitope suitable for use in the invention is from HIV gag (e.g., residues 262–278). One such sequence, designated GTH1, is YKRWIILGLNKIVRMYS (SEQ ID NO: 5) (from HIV p24 gag). Variants of this sequence can also be used. Alternatively, a carbohydrate such as the outer membrane protein of pneumococcus, or another carbohydrate or protein with immunogenic, T helper activity can be used.

The V3 components of the hybrid peptides present in the instant composition are selected so as to be representative of higher order structural motifs present in a population, which motifs mediate V3 functions in the course of envelope mediated HIV interaction with host cells. The Los Alamos National Laboratories Human Retroviruses and AIDS Database (Human Retroviruses and AIDS, 2000, Published by the Theoretical Biology and Biophysics G T-10, Mail Stop K710, LANL, Los Alamos, N. Mex.) presently contains over 14,000 HIV V3 envelope sequences, showing the extraordinary diversity the virus has obtained since originating in man in Africa approximately 50 years ago. For example, among 432 HIV-1 V3 sequences derived from individuals infected with subtype C (designated "Clade C") in Africa currently available in the HIV database, 176 distinct variants of a 23 amino acid stretch at the tip of the V3 loop have been found. Similarly, among 6870 B subtype (designated "Clade B") V3 sequences from the US, 1514 unique forms have been found.

A method has been developed to organize short antigenic domains by protein similarity scores using maximum-linkage clustering. This method enables the visualization of the clustering patterns as a dendrogram, and the splitting patterns in the dendrogram can be used to define clusters of related sequences (Korber et al, J. Virol, 68:6730–6744 (1994)). The method allows the use of several different amino acid similarity scoring schemes available in the literature, preferred is the amino acid substitution matrix developed by Henikoff and Henikoff (see Advances in Protein Chemistry 54:73–97 (2000) and Proteins: Structure, Function and Genetics 17:49–61 (1993)), designed to give substitutions that are well tolerated in conserved protein structural elements a high score, and a low score to those that are not. Typically excluded from consideration very rare, highly divergent peptides, and favored are peptides found in many individuals within the population. In a selected set of sequences, most of the unique forms are within one or two amino acids from a least one other of the peptides chosen. This method has been applied to clustering the large number of variants of the antigenic tip of the V3 domain within Clade B and Clade C into groups (about 25) that are likely to be cross-reactive within the group. Based on these clustering patterns, variants (e.g., about 25–30) are selected that are representative or "central" to each group, for testing for antigenicity. The HIV Clade B and Clade C gp120 envelope V3 sequences have been analyzed, as described above, for groups of V3 sequences predicted to have structural similarities. Twenty five Clade C and 30 Clade B groups have been defined, and chosen out of each group is a common, or the most common, sequence as a representative of that group. The selected V3 sequences have been included in a C4-V3 design thereby providing a 25 peptide Clade C immunogen, and a 30 peptide Clade B immunogen (see Tables 6 and 7).

TABLE 6

C4-V3 design of Clade C V3 sequences (SEQ ID NO: 6)
C4-V3-C1 KQIINMWQVVGKAMYA-trpnnntrksirigpGqtfyatg (SEQ ID NO: 7)
C4-V3-C2 KQIINMWQVVGKAMYA-trpnnntrksirigpGqtfyaRg (SEQ ID NO: 8)
C4-V3-C3 KQIINMWQVVGKAMYA-trpnnntrksirigpGqtfyaAg (SEQ ID NO: 9)
C4-V3-C4 KQIINMWQVVGKAMYA-IrpnnntrksVrigpGqtfyatg (SEQ ID NO: 10)
C4-V3-C5 KQIINMWQVVGKAMYA-trpnnntrksirigpGqtfFatg TABLE 6-continued C4-V3 design of Clade C V3 sequences C4-V3-C6   KQIINMWQVVGKAMYA-trpnnntrksirigpGqtfyatN   (SEQ ID NO: 11)

C4-V3-C7   KQIINMWQVVGKAMYA-trpnnntrEsirigpGqtfyatg   (SEQ ID NO: 12)

C4-V3-C8   KQIINMWQVVGKAMYA-trpnnntrRsirigpGqAfyatg   (SEQ ID NO: 13)

C4-V3-C9   KQIINMWQVVGKAMYA-trpnnntrkGirigpGqtfyatg   (SEQ ID NO: 14)

C4-V3-C10  KQIINMWQVVGKAMYA-trpSnntrksirigpGqAfyatg   (SEQ ID NO: 15)

C4-V3-C11  KQIINMWQVVGKAMYA-trpSnntrksirigpGqtfyatN   (SEQ ID NO: 16)

C4-V3-C12  KQIINMWQVVGKAMYA-trpSnntrEsirigpGqtfyatg   (SEQ ID NO: 17)

C4-V3-C13  KQIINMWQVVGKAMYA-trpnnntrksMrigpGqtfyatg   (SEQ ID NO: 18)

C4-V3-C14  KQIINMWQVVGKAMYA-trpGnntrksMrigpGqtfyatg   (SEQ ID NO: 19)

C4-V3-C15  KQIINMWQVVGKAMYA-trpGnntrksirigpGqtLyatg   (SEQ ID NO: 20)

C4-V3-C16  KQIINMWQVVGKAMYA-VrpnnntrksVrigpGqtSyatg   (SEQ ID NO: 21)

TABLE 6-continued

C4-V3 design of Clade C V3 sequences

C4-V3-C17  KQIINMWQVVGKAMYA-trpGnntrRsirigpGqtfyatg   (SEQ ID NO: 22)

C4-V3-C18  KQIINMWQVVGKAMYA-IrpGnntrksVrigpGqtfyatg   (SEQ ID NO: 23)

C4-V3-C19  KQIINMWQVVGKAMYA-trpnnntrksirigpGqAfyatN   (SEQ ID NO: 24)

C4-V3-C20  KQIINMWQVVGKAMYA-trpnnntrQsirigpGqAfyatK   (SEQ ID NO: 25)

C4-V3-C21  KQIINMWQVVGKAMYA-trpGnntrksirigpGqAfFatg   (SEQ ID NO: 26)

C4-V3-C22  KQIINMWQVVGKAMYA-trpGnntrksVrigpGqAfyatN   (SEQ ID NO: 27)

C4-V3-C23  KQIINMWQVVGKAMYA-trpnnntrkGiHigpGqAfyaAg   (SEQ ID NO: 28)

C4-V3-C24  KQIINMWQVVGKAMYA-trpnnntrkGiGigpGqtfFatE   (SEQ ID NO: 29)

C4-V3-C25  KQIINMWQVVGKAMYA-trpGnntrEsiGigpGqAfyatg   (SEQ ID NO: 30)

TABLE 7

C4-V3 peptides Clade B

| | | |
|---|---|---|
| C4-V3-396.2  | KQIINMWQVVGKAMYA-RPNNNTRRNIHIGLGRRFYAT-* | (SEQ ID NO: 31) |
| C4-V3-170.6  | KQIINMWQVVGKAMYA-RPNNNTRRSVRIGPGGAMFRTG* | (SEQ ID NO: 32) |
| C4-V3-82.15  | KQIINMWQVVGKAMYA-RPNNNTRRSIPIGPGRAFYTTG* | (SEQ ID NO: 33) |
| C4-V3-144.8  | KQIINMWQVVGKAMYA-RPDNNTVRKIPIGPGSSFYTT-* | (SEQ ID NO: 34) |
| C4-V3-23.38  | KQIINMWQVVGKAMYA-RPIKIERKRIPLGLGKAFYTTK* | (SEQ ID NO: 35) |
| C4-V3-365.2  | KQIINMWQVVGKAMYA-RPSNNTRKGIHLGPGRAIYATE | (SEQ ID NO: 36) |
| C4-V3-513.2  | KQIINMWQVVGKAMYA-RPSNNTRKGIHMGPGKAIYTTD | (SEQ ID NO: 37) |
| C4-V3-1448.1 | KQIINMWQVVGKAMYA-RPGNTTRRGIPIGPGRAFFTTG | (SEQ ID NO: 38) |
| C4-V3-69.18  | KQIINMWQVVGKAMYA-RPNNNTRKSIRIGPGRAVYATD | (SEQ ID NO: 39) |
| C4-V3-146.8  | KQIINMWQVVGKAMYA-RPGNNTRRRISIGPGRAFVATK | (SEQ ID NO: 40) |
| C4-V3-113.1  | KQIINMWQVVGKAMYA-RPNNNTRRSIHLGMGALYATG-* | (SEQ ID NO: 41) |
| C4-V3-51.23  | KQIINMWQVVGKAMYA-RPSNNTRRSIHMGLGRAFYTTG-* | (SEQ ID NO: 42) |
| C4-V3-72.18  | KQIINMWQVVGKAMYA-RPNNNTRKGINIGPGRAFYATG-* | (SEQ ID NO: 43) |
| C4-V3-36.29  | KQIINMWQVVGKAMYA-RPNNNTRKGIHIGPGRTFFATG-* | (SEQ ID NO: 44) |
| C4-V3-70.18  | KQIINMWQVVGKAMYA-RPNNNTRKRIRIGHIGPGRAFYATG* | (SEQ ID NO: 45) |

TABLE 7-continued

C4-V3 peptides Clade B

| | | |
|---|---|---|
| C4-V3-89.14 | KQIINMWQVVGKAMYA-RPSINKRRHIHIGPGRAFYAT-* | (SEQ ID NO: 46) |
| C4-V3-163.7 | KQIINMWQVVGKAMYA-RLYNYRRKGIHIGPGRAIYATG* | (SEQ ID NO: 47) |
| C4-V3-57.20 | KQIINMWQVVGKAMYA-RPNRHTGKSIRMGLGRAWHTTR* | (SEQ ID NO: 48) |
| C4-V3-11.85 | KQIINMWQVVGKAMYA-RPNNNTRKSINIGPGRAFYTTG---* | (SEQ ID NO: 49) |
| C4-V3-34.29 | KQIINMWQVVGKAMYA-RPNNNTRKSIQIGPGRAFYTTG---* | (SEQ ID NO: 50) |
| C4-V3-1.481 | KQIINMWQVVGKAMYA-RPNNNTRKSIHIGPGRAFYTTG---* | (SEQ ID NO: 51) |
| C4-V3-85.15 | KQIINMWQVVGKAMYA-RPNNNTRKSIHIAPGRAFYTTG---* | (SEQ ID NO: 52) |
| C4-V3-62.19 | KQIINMWQVVGKAMYA-RPNNNTRKSIHIGPGRAFYATE------* | (SEQ ID NO: 53) |
| C4-V3-125.9 | KQIINMWQVVGKAMYA-RPNNNTRRRISMGPGRVLYTTG* | (SEQ ID NO: 54) |
| C4-V3-35.29 | KQIINMWQVVGKAMYA-RPNNNTRKRISLGPGRVYYTTG* | (SEQ ID NO: 55) |
| C4-V3-74.17 | KQIINMWQVVGKAMYA-RPNNNTRKRMTLGPGKVFYTTG* | (SEQ ID NO: 56) |
| C4-V3-46.26 | KQIINMWQVVGKAMYA-RPDNTIKQRIIHIGPGRPFYTT-* | (SEQ ID NO: 57) |
| C4-V3-122.9 | KQIINMWQVVGKAMYA-RPNYNETKRIRIHRGYGRSFVTVR* | (SEQ ID NO: 58) |
| C4-V3-162.7 | KQIINMWQVVGKAMYA-RPGNNTRGSIHLHPGRKFYYSR* | (SEQ ID NO: 59) |
| C4-V3-3.323 | KQIINMWQVVGKAMYA-RPNNNTRKSINMGPGRAFYTTG | (SEQ ID NO: 60) |

While the above is offered by way of example, it will be appreciated that the same analyses can by performed for HIV Clades A, D, E, F, G, H, M, N, O, etc, to design V3 immunogens that react with HIV primary isolates from these Clades.

Figure 3:
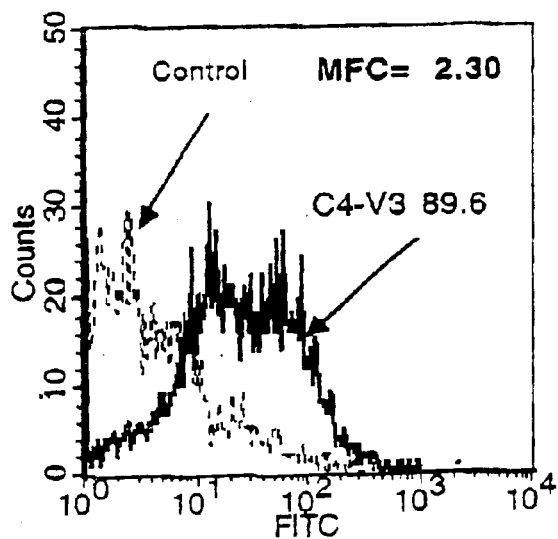
FIG. 3: C4$_{E9V}$-V389.6 peptides bound better to human PB lymphocytes and monocytes than did the C4-V3 89.6 peptides. Similar data were obtained with the C4-V3 89.6P and C4-E9V-89.6P peptides. Sequence of the C4-V389.6 peptide form HIV89.6 isolate was: KQIINMWQEVGKAMYA-TRPNNNTRRRLSIGPGRAFYARR (SEQ ID NO: 1); the sequence of the C4$_{E9V}$-V389.6 peptide was: KQIINMWQVVGKAMYA-TRPNNNTRRRLSIGPGRAFYARR (SEQ ID NO: 2); the sequence of the C4-V389.6P peptide was: KQIINMWQEVGKAMYA-TRPNNNTRERLSIGPGRAFYARR (SEQ ID NO: 3); the sequence of the C4E9V-V389.6P peptide was: KQIINMWQVVGKAMYA-TRPNNNTRERLSIGPGRAFYARR (SEQ ID NO: 4).
Figure 3:
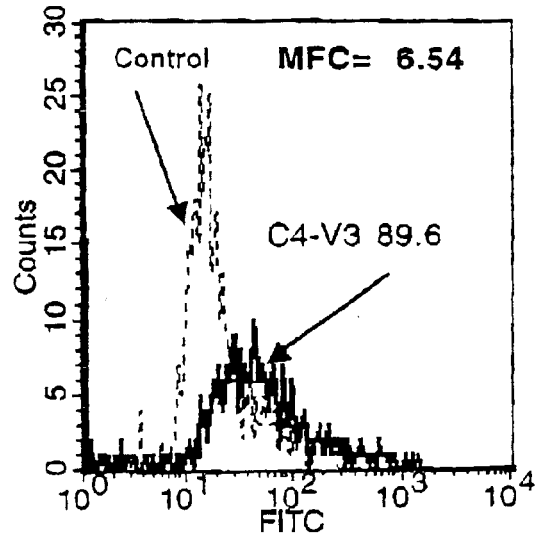
Figure 3:
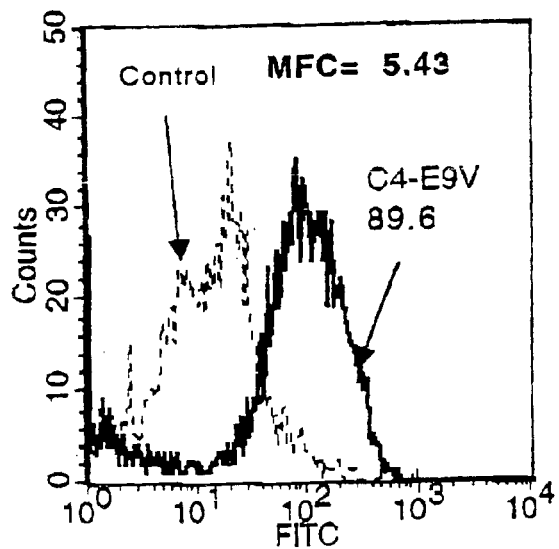
Figure 3:
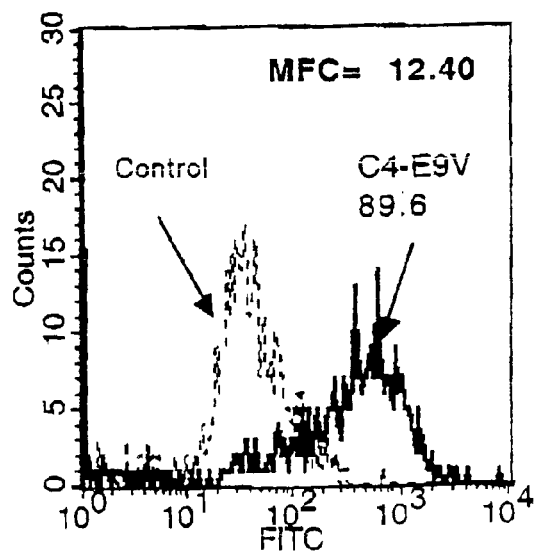

In addition to the sequences described in Tables 6 and 7, a substitution has been made in the C4 sequence at position 9 from E to V to enhance the binding of the C4 region to human immune cell membranes, and to increase immunogenicity (see Example that follows). Substituting V for E at position 9 of C4 results in the C4-E9V-V3RF(A) peptide inducing 2–3 logs higher anti-gp 120 V3 region antibody levels compared with the original C4-V3RFA(A) peptide. The effect of the E9V substitution is not species specific. While not wishing to be bound by theory, the data may indicate that the ability of the E9V variant peptide to enhance B cell antibody production is not MHC specific but rather it relates in some manner to non-MHC specific factors, such as the ability of the peptides to bind to the lipid bilayer of immune cells. The data presented in FIG. 3 demonstrate the ability of $C4_{E9V}$-V389.6 peptides to bind to human PB lymphocytes and monocytes. The ability of the C4 and C4E9V "T helper" determinants to facilitate immunogenicity of the V3 region may be due to the ability of helical amphipathic structures to interact with lipid bilayers in a non-MHC related manner and promote peptide internalization. The invention encompasses the use of C4 sequences in addition to those described above.

The peptide immunogens of the invention can be chemically synthesized and purified using methods which are well known to the ordinarily skilled artisan. (See, for example, the Example that follows.) The composition can comprise the peptides linked end to end or can comprise a mixture of individual peptides. The peptide immunogens can also be synthesized by well-known recombinant DNA techniques. Recombinant synthesis may be preened when the peptides are covalently linked.

Nucleic acids encoding the peptides of the invention can be used as components of a DNA vaccine wherein the peptide encoding sequence(s) is/are administered as naked DNA or, for example, a minigene encoding the peptides can be present in a viral vector, such as an adenoviral vector, a modified vaccinia ankara vector, a vaccinia vector or an attenuated TB vector. Expression of the immunogenic peptides of the invention can be induced in a patient's own cells, by introduction into those cells of nucleic acids that encode the peptides, preferably using codons and promoters that optimize expression in human cells. Examples of methods of making and using DNA vaccines are disclosed in U.S. Pat. Nos. 5,580,859, 5,589,466, and 5,703,055.

The composition of the invention comprises an immunologically effective amount of the peptide immunogens of this invention, or DNA sequence(s) encoding same, in a pharmaceutically acceptable delivery system. The compositions can be used for prevention and/or treatment of immunodeficiency virus infection. The compositions of the invention can be formulated using adjuvants, emulsifiers, pharmaceutically-acceptable carriers or other ingredients routinely provided in vaccine compositions. Optimum formulations can be readily designed by one of ordinary skill in the art and can include formulations for immediate release and/or for sustained release, and for induction of systemic immunity and/or induction of localized mucosal immunity (e.g, the formulation can be designed for intranasal administration). The present compositions can be administered by any convenient route including subcutaneous, intranasal, oral, intramuscular, or other parenteral or enteral route. The immunogens can be administered as a single dose or multiple doses. Optimum immunization schedules can be readily determined by the ordinarily skilled artisan and can vary with the patient, the composition and the effect sought. By way of example, it is noted that approximately 50 µg–100 µg of each hybrid peptide can be administered, for example, intramuscularly (e.g. 3×).

The invention contemplates the direct use of both the peptides of the invention and nucleic acids encoding same. For example, a minigene encoding the peptides can be used as a prime and/or boost.

In addition to the composition described above, the invention encompasses each of the hybrid peptides disclosed as well as each of the components (C4 and V3), alone or in covalent or non-covalent association with other sequences. The invention further encompasses nucleic acid sequences encoding any and all such peptides.

Certain aspects of the invention can be described in greater detail in the non-limiting Example that follows.

EXAMPLE 1

Experimental Details

Peptide Design, Synthesis and Purification.

Peptides were designed, as shown in Table 1. It was hypothesized that alteration of the C4 sequence to reduce its helical conformational tendency in peptides might cause enrichment of solution conformers resembling a β strand conformation. This in turn might cause C4 to be immunogenic for antibodies recognizing the native conformation of the C4 (part of the CD4 binding site) region of gp120. The present work describes tests of this hypothesis in chimeric peptide C4-V3 RF, which has a V3 segment from gp120 of HIV strain RF, and three sequence variants wherein single amino-acid replacements have been introduced at position 9 in the C4 segment, Glu (E) to Gly (G), Glu (E) to Val (V), and at position 12, Lys (K) to Glu (E) (Table 1). These replacements were made in part to disrupt possible stabilization of helical conformations due to side-chain (i, i+3) charge interaction between E9 and K12 (Scholtz et al, Biochemistry 32:9668–9676 (1993)). In addition, the substitution in $C4_{E9G}$-V3RF(A) was expected to disfavor helix formation by introducing greater main-chain flexibility (Chakrabartty et al, Adv. Protein Chem. 46:141–176 (1995)). Furthermore the substitution in $C4_{E9G}$-V3RF(A) introduced two adjacent valine residues which has been hypothesized to favor extended conformations. Thus, the parent peptide, C4-V3RF(A) (Haynes et al, AID Res. Human Retroviruses 11:211–221 (1995)) contained 16 N-terminal residues from the C4 domain of $gp120_{IIIB}$ and 23 C-terminal residues from the V3 domain of gp120 of HIVRF.

Peptides were synthesized by fluorenylmethoxycarbonyl chemistry on an ABI 43 1A peptide synthesizer (Applied Biosystems, Inc., Foster City, Calif.), then purified by reverse-phase high performance liquid chromatography. The purity and identity of the product were confirmed by determining molecular mass by electrospray mass spectrometry.

Immunization Methods.

Mice were immunized with 50 μg of the indicated peptide in incomplete Freund's adjuvant (1SA51, Seppic Inc., Paris France) at weeks 0, 3, and 7 and bled at weeks 2, (bleed 1 after boost 1), week 5 (bleed 2 after boost 2) and week 8 (bleed 3 after boost 3). Immune responses were seen after bleed 2 in most animals and data are reported from bleeds 2 and 3.

Guinea pigs were immunized intranasally with 200 μg of C4-V3 peptide in saline with 1 μg of cholera toxin as adjuvant as described. Guinea pigs were immunized on day 0, day 14 and day 21 and serum samples before and 1 week following each immunization obtained by cardiac puncture.

ELISA Assay.

Anti-HIV env peptide ELISA assays were performed as previously described (Haynes et al, J. Immunol. 151:1646–1653 (1993), Haynes et al, AID Res. Human Retroviruses 11:211–221 (1995)).

Splenocyte Proliferation Assay.

Mouse splenocyte proliferation assay using $^3$H-thymidine incorporation was performed as previously described (Haynes et al, AID Res. Human Retroviruses 11:211–221 (1995)).

Neutralizing Antibody Assays.

Assays for ability of anti-HIV antisera to neutralize HIV were performed as described (Palker et al, J. Immunol. 142:3612–3619 (1989), Haynes et al, Trans. Am. Assoc. Physician 106:31–41 (1993), Haynes et al, J. Immunol. 151:1646–1653 (1993), Haynes et al, AID Res. Human Retroviruses 11:211–221 (1995)).

NMR Spectroscopy.

Peptides were dissolved to 4 mM in a solution of 90% $^1H_2O$, 10% $^2H_2O$, 20 mM NaCl, 5 mM $KH_2PO_4$, 1 mM sodium azide, 0.5 mM sodium 3-(trimethylsilyl) propionate, at a pH of 4.2. The methyl resonance of the latter component served as a chemical shift reference.

Spectra of samples prepared in this way were acquired with a Varian Unity 500 MHz spectrometer at a temperature of 278 K. The lock signal was from deuterium in the sample.

TABLE 1

Peptides Used in This Study

| Peptide | C4 | V3 |
|---|---|---|
| | 1                16 | 17                          39 |
| C4-V3RF(A) | KQIINMWQEVGKAMYA | TRPNNNTRKSITKGPGRVIYATG (SEQ ID NO: 61) |
| $C4_{E9G}$-V3RF(A) | KQIINMWQGVGKAMYA | TRPNNNTRKSITKGPGRVIYATG (SEQ ID NO: 62) |
| $C4_{E9V}$-V3RF(A) | KQIINMWQVVGKAMYA | TRPNNNTRKSITKGPGRVIYATG (SEQ ID NO: 63) |
| $C4_{K12E}$-V3RF(A) | KQIINMVWQVVGKAMYA | TRPNNNTRKSITKGPGRVIYATG (SEQ ID NO: 64) |

All sequences from Los Alamos National Laboratory AIDS Sequence Database.

The following two-dimensional spectra were obtained: (a) double-quantum-filtered correlation spectroscopy (DQF-COSY) (Piantini et al, J. Am. Chem. Soc. 104:6800–6801 (1982), Rance et al, Biochem. Biopjys. Res. Commun. 117:479–485 (1983)); (b) total correlation spectroscopy (TOCSY) (Bax et al, J. Magn. Reson. 65:355–360 (1985), Levitt et al, J. Magn. Reson. 47:328–330 (1982)) with a mixing time of 150 ins; and (c) nuclear Overhauser exchange spectroscopy (NOESY) (Jeener et al, J. Phys. Chem. 71:4546–4553 (1979)) with a mixing time of 300 ins. Water resonance was suppressed by selective saturation during the relaxation delay, and, for NOESY, during the mixing period. The spectral width was 6700 Hz, with the indirectly acquired dimension collected as 750 (COSY), 512 (TOCSY), or 350 (NOESY) complex increments; and the directly acquired dimension containing 1024 complex points. Data were processed with FELIX 2.3 software (Biosym, San Diego, Calif.). Directly acquired free-induction decays were corrected for base-line offset. Decays in both dimensions were multiplied by a sinebell-squared function (phase shifted by 75°) and zero-filled to 2048 points before Fourier-transformation.

Peptide Membrane Binding Assay.

Peptides at 100 ng/ml were incubated with 106 peripheral blood mononuclear cells for 1 hour at 4° C., washed ×3 with phosphate buffered saline PHz 7.0, contained 0.1% sodium azide, then incubated guinea pig anti-HIV 89.6 V3 antisera (×1 hr) (Liao et al, J. Virol. 74:254–263 (2000)), wash as above and then incubated with FITC-conjugated goat anti-guinea pig IgG. After a final wash as alone, the cells were analyzed for the relative amount of peptide bound to either PB lymphocytes or PB monocytes as reflected in the mean fluorescent channel (MFC) of reactivity of the anti-HIV 89.6 V3 antisera.

Results

Anti-gp120 V3 Antibody Responses Following Immunization of Mice with C4-V3RF, $C4_{E9V}$-V3RF(A), $C4_{E9G}$-V3RF(A) and $C4_{K12E}$-V3RF(A) Peptides.

First, the ability of C4-V3HIVRF variants to modulate the immunogenicity of the peptide with regard to antibodies to the V3 portion of the C4-V3 immunogen were assayed. The results (FIG. 1, Table 2) show differences among the four peptides in their ability to induce anti-HIVRF V3 antibody responses. Sera from $C4_{E9V}$-V3RF(A)-immunized mice had a log higher anti-V3 antibody titer than either mice immunized with the native C4-V3RF(A) peptide or the C4E9V-V3RF(A) peptide variant. After one immunization, no anti-V3RF antibody response was seen in mice immunized with either C4-V3RF(A), $C4_{E9G}$-V3RF(A), or $C4_{K12E}$-V3RF(A) peptides. However, after only one immunization with 50 μg of the $C4_{E9V}$-V3 peptide, the geometric mean titer to V3RF (A) peptide was 1:5012 (n=3 mice), with titers of 1:3200, 1:3200 and 1:12,800 in each of the three mice tested, respectively. Thus, the E9V C4-V3RF(A) variant induced a higher titer and earlier anti-gp 120 V3 antibody responses than the other C4-V3RF(A) peptides tested. After 2 boosts, $C4_{E9V}$-V3RF(A)-immunized mice had 2 logs higher anti-V3 antibody responses than did C4-V3RF(A) immunized mice (FIG. 1, Table 2).

TABLE 2

Comparison of the Ability of C4-V3 Peptides To Induce HIV gp120 Anti-C4 and Anti-V3 Antibodies in Balb/c Mice

| Peptide Immunogen | Number of Animals | C4 | V3RF(A) | C4-V3RF(A) | C4E9G-V3RF(A) | C4E9V-V3RF(A) | C412EV3RF(A) |
|---|---|---|---|---|---|---|---|
| | Geometric Mean Titer | | | | | | |
| C4-V3RF(A) | 6 | 2 | 1,584 | 2,239 | 1,195 | 1,584 | 1,412 |
| $C4_{E9G}$-V3RF(A) | 6 | 2 | 6,310 | 7,079 | 5,623 | 3,162 | 3,548 |
| $C4_{E9V}$-V3RF(A) | 5 | 14 | 151,356 | 131,825 | 87,096 | 87,096 | 114,815 |
| $C4_{K12E}$-V3RF(A) | 6 | 1 | 8 | 8 | 1 | 3 | 3 |

Data represent the reciprocal of endpoint dilutions at which the E/C was ≧3.0 in anti-peptide ELISA after two immunizations.

The $C4_{K12E}$-V3RF(A) peptide variant induced anti-V3 antibody responses 3 logs lower than the C4-V3RF(A) peptide after 2 immunizations (FIG. 1, Table 2). Thus, single amino-acid replacements in the C4 T helper region had extraordinary effects on immunogenicity of the HIVRF gp120 V3 domain.

Comparison of the Ability of C4-V3RF(A) Peptides to Induce Anti-HIV gp120 Peptide 3H-Thymidine Incorporation in Splenocytes from Naive and Peptide-Immunized Mice.

Next, C4-V3 peptides were tested for their ability to stimulate proliferation of splenocytes from peptide-immunized mice. Balb/c mice were sacrificed after the third peptide immunization and their splenocytes assayed for the ability to proliferate to PHA and to each peptide type (Table 3). It was found that C4-V3RF(A), $C4_{E9V}$-V3RF(A), and $C4K_{K12E}$-V3RF(A) peptides all induced in vitro proliferative responses to the immunizing peptides, whereas the $C4_{E9G}$-V3RF(A) variant peptide did not induce proliferative responses in E9G-primed mice significantly over responses of naive mice (Table 3). Regarding the ability of the E9V peptide variant to induce earlier and greater anti-V3 antibody responses compared to the other peptides tested, the $C4_{E9V}$-V3RF(A) peptide-primed splenocytes for proliferation to the immunizing peptide only minimally better than did each of the other three peptides (Table 3). Thus, altered induction of T helper cell proliferative responses did not explain the differences in peptide immunogenicity.

TABLE 3

Comparison of the Ability of C4-V3 Peptides To Induce Anti-HIV gp120 Peptide $^3$H-Thymidine Incorporation in Splenocytes from Naïve and Immunized Mice

| Peptide Immunogen | N | Peptide Used As Stimulator in $^3$H-Thymidine Incorporation Assay | | | | | |
|---|---|---|---|---|---|---|---|
| | | C4 | V3RF(A) | C4-V3RF(A) | C4$_{E9G}$-V3RF(A) | C4$_{E9V}$-V3RF(A) | C4$_{K12E}$-V3RF(A) |
| | | Mean ± SEM Δ CPM per 10$^6$ Splenocytes in Culture | | | | | |
| None (Naïve Balb/c) | 6 | 613 ± 322 | 408 ± 140 | 149 ± 84 | 114 ± 85 | 74 ± 47 | 187 ± 165 |
| C4-V3RF(A) | 6 | 2,289 ± 1,332 | 955 ± 353 | 8,390 ± 1,424$^a$ | 8,067 ± 1,728 | 6,242 ± 1,787 | 6,198 ± 1,343 |
| C4$_{E9G}$-V3RF(A) | 6 | 408 ± 95 | 708 ± 325 | 2,103 ± 1,170 | 3,559 ± 2,310$^b$ | 988 ± 340 | 1,101 ± 399 |
| C4$_{E9V}$-V3RF(A) | 5 | 84 ± 52 | 1,463 ± 473 | 933 ± 4,528 | 11,743 ± 3,830 | 24,824 ± 5,581$^c$ | 10,269 ± 3,592 |
| C4$_{K12E}$-V3RF(A) | 6 | 3,430 ± 2,796 | 4,417 ± 2,217 | 8,670 ± 3,865 | 13,237 ± 8,563 | 7,513 ± 2,951 | 12,644 ± 4,138$^d$ |

Data represent peak 3H-thymidine responses at 7 days.
Δ CPM = CPM experimental − experimental − experimental control.
$^a$p < .001 vs naïve mice; p = NS vs C4-V3RF(A) or C4K12E-V3RF(A) stimulated C4K12E-V3RF(A) immunized splenocytes.
$^b$p = NS vs naïve mice.
$^c$p < .001 vs naïve mice.
$^d$p < .02 vs naïve mice.

The lower antibody titer induced by the C4$_{K12E}$-V3 peptide against V3RF(A) was not an artifact attributable to lack of ability of the V3 peptide not binding to the ELISA plate, as sera from C4$_{E9V}$-V3RF(A)-induced antisera had high reactivity to the V3RF(A) peptide on the ELISA plate. Similarly, the C4$_{K12E}$-V3RF(A) peptide could bind anti-V3RF antibody, as multiple antisera raised against C4-V3 peptides bound the C4$_{K12E}$-V3 variant (Table 2).

Antibody levels to the C4 region were also tested. The C4 region induced only a minimal antibody response compared to the V3 region, with all the C4-V3 peptides tested (Table 2).

Anti-gp 120 V3 Antibody Responses Following Immunization of Guinea Pigs.

Next, 2 guinea pigs were immunized each with 200 μg of C4-V3RF(A), C4$_{E9G}$-V3 RF(A), C4$_{E9V}$-V3 RF(A) or C4$_{K12E}$-V3 RF(A) peptide intranasally with 1 μg cholera toxin adjuvant in saline. Intranasal immunization of peptides with cholera toxin has been previously shown to result in CTL and titers of anti-peptide antibody similar in levels to titers induced by initial antigens administered subcutaneously or intramuscularly in oil in water adjuvants such as complete and incomplete Freund's adjuvant. In addition, it was desirable to determine the ability of C4-V3 peptides in an aqueous solution (such as in saline for intranasal immunization) to induce anti-HIV antibody responses in order to correlate reactivity of antibodies generated against peptide in an aqueous adjuvant with peptide conformers solved in an aqueous solution. Finally, there was interest in determining if the amino acid substitutions in the C4 region conferred on the C4-V3 peptides the same pattern of immunogenicity as seen in oil in water adjuvant in mice.

It was found that after 2 immunizations the C4-V3 RF(A) peptide induced a mean anti-HIV peptide antibody titer of 3981, peptide induced titers of 1 log (GMT=31,623) higher. As in mice, substituting the Glu (E) for Lys (K) at position 12 in the C4 peptide abrogated peptide immunogenicity in guinea pigs (GMT=16) (Table 4).

TABLE 4

Titers of C4-V3 HIV Envelope Antibodies Induced by C4-V3RF(A) Peptides in Guinea Pigs

| Immunizing Peptide | Titer Against Immunizing Peptide* |
|---|---|
| C4-V3RF(A) | 3,981 |
| C4-$_{E9G}$-V3RF(A) | 2,818 |
| C4-$_{E9V}$-V3RF(A) | 31,623 |
| C4-$_{K12E}$-V3RF(A) | 16 |

*Data represent the mean titers from 2 animals after 2–3 immunizations intranasally with 400 ug of the indicated peptide formulated in saline with cholera toxin as an adjuvant.

Ability of Antibodies Against C4-V3 Peptides to Induce Neutralizing Antibodies.

In order to induce high levels of neutralizing antibodies with C4-V3 peptides, usually 5 immunizations are given (Palker et al, J. Immunol. 142:3612–3619 (1989), Haynes et al, J. Imnunol. 151:1646–1653 (1993), Palker et al, Proc. Natl. Acad. Sci. USA 85:1932–1936 (1988), Liao et al, J. Virol. 74:254–263 (2000)). The guinea pig sera from the experiment presented in Table 4 were tested for ability to neutralize HIVRF. It was found that one sera from the C4-V3RF(A)-immunized animals (after 3 injections) had a neutralizing antibody titer of 1:40 against HIVRF, while one animal of the C4$_{E9V}$-V3RF(A)-injected animals had a neutralizing titer of 1:340 after only 2 injections. Thus, antibodies induced by the C4$_{E9V}$-V3RF(A) peptide can bind to native gp120 and neutralize HIVRF.

Inability of the C4-E9V-RF(A) Sera to Bind to gp120 from HIV$_{IIIB}$.

The V3 loop sequence of HIV$_{IIIB}$ is different from that of HIVRF, and thus HIVRF anti-V3 neutralizing antibodies do not neutralize HIV$_{IIIB}$. To determine if any antibodies were generated by any of the C4-V3RF(A) variant peptides, all the mouse sera in Table 2 were tested, as were the guinea pig sera in Table 4, for the ability to bind to native recombinant HIV$_{IIIB}$ gp120 in ELISA. Since anti-HIVRF V3 antibodies do not bind to the HIV$_{IIIB}$ V3 loop, any binding activity of these anti-C4-V3 sera would be to the C4 region of HIV$_{IIIB}$, which is conserved between HIV$_{IIIB}$ and HIVRF. No binding of any mouse or guinea pig anti-C4-V3 sera to HIV$_{IIIB}$ gp120 was seen, indicating the inability of these peptides to induce antibodies against the native gp120 C4 region.

Conformational Propensities of C4-V3 RF Sequence Variants in Aqueous Solution.

Next, the peptides were examined by NMR to determine whether conformational changes had been induced by amino-acid sequence alteration. It was hypothesized that specific amino-acid substitutions in the C4 segment would lead to a decrease in the tendency of this region to adopt transient helical conformations. To test this hypothesis, each of the four peptides, C4-V3RF and variants E9G, E9V and K12E, was subjected to $^{1}$H NMR spectroscopy to assign resonances and to analyze nuclear Overhauser effects between hydrogen nuclei on separate residues.

Resonance assignments for nearly all $^{1}$H were determined from TOCSY, DQF-COSY, and NOESY spectra by standard methods (Wuthrich, NMR of Proteins and Nucleic Acids, John Wiley and Sons, New York (1986)), and are shown in FIG. 2. The value of the chemical shift for a main-chain $^{1}$H, for example, the a carbon $C^{a}$H, is correlated with secondary structure in the case of proteins or well structured peptides (Wishart et al, J. Mol. Biol. 222:311–333 (1991)). Hence, strong tendencies among C4-V3RF peptides to adopt secondary structure in solution may be manifested in chemical shift values. This was examined by calculating for each peptide the difference in chemical shift between the C—H of each residue and a shift value representing the average for all secondary structures in proteins (Wishart et al, J. Mol. Biol. 222:311–333 (1991)). In no peptide were there stretches of sequence with high or low values of the chemical shift difference that would be evidence of stable secondary structure, for example helix or β strand.

NMR parameters such as chemical shift and coupling constants are often insensitive indicators of weak preferences for particular conformations since their values are the average of the entire population, thus obscuring the contribution of a slight bias for populating certain conformations. The nuclear Overhauser effect (NOE) is often more sensitive at revealing conformational propensities because it may give rise to a unique signal, although weak, on a background consisting only of random noise. Hence, NOESY spectra of C4-V3RF and its variants were characterized to identify each signal and evaluate its relative intensity. Sequential and medium range NOEs involving main-chain NH or CaH are listed in FIG. 2. These NOEs and the possible conformational propensities they represent are discussed as follows for $C4_{E9G}$-V3RF(A) and $C4_{E9V}$-V3RF(A). Variant $C4_{K12E}$-V3RF(A)K12E is discussed separately below because it was studied under different conditions.

In terms of overall conformation, all four peptides showed NOE patterns suggesting no tendency to adopt stable structure. For example, sequential daN(i, i+1) and dNN(i, i+1) NOEs were usually both present for each sequential pair of residues, with the former typically more intense, indicating that f and j main-chain dihedral bond angles varied and maintained on average an extended conformation (Dyson et al, Ann. Rev. Biophys. Chem. 20:519–538 (1991)). Also the absence of long range NOEs [(i, i+5) or greater] and the few and generally weak medium-range NOEs suggested no significant population of higher order structure.

However, the fact that some medium range NOEs were detected is evidence of propensity to adopt non-random conformations in certain regions (Dyson et al, Ann. Rev. Biophys. Chem. 20:519–538 (1991)). Although only one mixing time was used for NOESY spectra (300 ins), previous studies of a related C4-V3 RF peptide (de Lorimier et al, Biochemistry 33:2055–2062 (1994)) showed that medium range NOEs were still observable at shorter (75 and 150 ins) mixing times. Hence, the NOEs indicating medium range interactions are not likely due to spin-diffusion.

Within the C4 segment C4-V3RF and $C4_{E9V}$-V3RF(A) showed numerous medium range NOEs which are consistent with a tendency of this region to populate nascent helical conformations. The presence of contiguous or overlapping daN(i,i+2) NOEs from $Trp^{7}$to $Tyr^{15}$(C4-V3RF) and from $Ile^{4}$ to $Lys^{12}$ (E9V) indicates a propensity for nascent helical turns in these regions (Dyson et al, Ann. Rev. Biophys. Chem. 20:519–538 (1991), Dyson et al, J. Mol. Biol. 201:201–217 (1988)). A dNN(i,i+2) NOE in this region in C4-V3 RF (between $Lys^{12}$ and $Met^{14}$) is also consistent with main-chain f and j dihedral angles representative of helical turns (Dyson et al, Ann. Rev. Biophys. Chem. 20:519–538 (1991)). C4-V3 RF shows three consecutive daN(i,i+3) NOEs from residues $Val^{10}$ to $Tyr^{15}$, which is highly indicative of full helical turns. The presence of equivalent NOEs in E9V could not be ascertained due to overlap with other NOEs. However both C4-V3RF and E9V show two dab(i, i+3) NOEs, between $Val^{10}$ and $Ala^{13}$ and between $Ala^{13}$ and $Met^{14}$. This type of NOE is also highly suggestive of full helical turns in these regions of C4.

Variant $C4_{E9G}$-V3RF(A)on the other hand showed no evidence, in terms of medium range NOEs, for preferential population of certain conformations in C4. This absence of medium range NOEs was not due merely to ambiguities caused by signal overlap, because there were at least five positions where an NOE was unambiguously absent in $C4_{E9G}$-V3RF(A), but present in the parent peptide C4-V3 RF. Thus, the E to G substitution in the C4 peptide appeared to prevent helical conformer formation in the peptide.

In the V3 segment of the three peptides, C4-V3 RF, $C4_{E9G}$-V3RF(A) and $C4_{E9V}$-V3RF(A), were medium range NOEs suggesting preferred solution conformations in certain RE regions. All three peptides showed evidence of a reverse turn in the sequence $Arg^{18}$-$Pro^{19}$-$Asn^{20}$-$Asn^{21}$, where these residues comprised positions 1 to 4, respectively, of the turn. The NOE pattern consistent with a reverse turn included a weak dNd(i,i+1) between $Arg^{18}$ and $Pro^{19}$, undetectable ddN(i,i+1) between $Pro^{19}$ and $Asn^{21}$, weak dad(i,i+1) between $Arg^{18}$ and $Pro^{19}$, strong daN(i,I+1) between $Pro^{19}$ and $Asn^{20}$, and detectable daN(i,i+2) between $Pro^{19}$ and $Asn^{21}$ (Dyson et al, J. Mol. Biol. 201:161–200 (1988)). The detection of the weak dNd(i,i+1) NOE ($Arg^{18}$to $Pro^{19}$) suggested that a Type I turn may be the preferred conformation (Dyson et al, J. Mol. Biol. 201:161–200 (1988)).

All three peptides also showed evidence of preferred conformers at the sequence $Ser^{26}$-$Ile^{27}$-$Thr^{28}$-$Lys^{29}$. There were two consecutive daN(i,i+2) NOEs, between $Ser^{26}$ and $Thr^{28}$ and between $11e^{27}$ and $Lys^{29}$, as well as medium range NOEs not shown in FIG. 2. The latter included a dbN(i,i+2) NOE between $Ser^{26}$ and $Thr^{28}$, and a dba(i,i+2) NOE between these same residues. The conformational preferences giving rise to these NOEs did not fit a typical secondary structure, and suggested an unusual turn that placed the side-chain of $Ser^{26}$ in close proximity to the main-chain groups of $Thr^{28}$. This type of conformation has been described as a kink in the context of a helical region (Osterhout et al, Biochemistry 28:7059–7064 (1989)).

A third conformational feature in the V3 segments of C4-V3RF, $C4_{E9V}$-V3RF(A) and $C4_{E9G}$-V3RF(A)occurred in the sequence $Gly^{30}$-$Pro^{31}$-$Gly^{32}$-$Arg^{33}$. In E9G the NOEs between these residues resembled the pattern described above that was consistent with a reverse turn (Dyson et al, J. Mol. Biol. 201:161–200 (1988)). This included a weak dNd(i,i+1) NOE between $Gly^{30}$ and $Pro^{31}$, a weak ddN(i, i-I-i) NOE between $Pro^{31}$ and $Gly^{32}$, a weak dad(i,i+1) NOE between $Gly^{30}$ and $Pro^{31}$, a strong daN(i,i+1) NOE between $Pro^{31}$ and $Gly^{32}$, and a detectable daN(i,i+2) NOE between $Pro^{31}$ and $Arg^{33}$. In the C4-V3RF peptide, the pattern of (i,i+1) NOE intensities was the same but no daN(i,i+2) NOE was detected between Pro$^{31}$ and Arg$^{33}$. Instead a daN(i,i+2) NOE was detected between Gly$^{30}$ and Gly$^{32}$. And in C4-E9V V3RF, both daN(i,i+2) NOEs, Gly$^{30}$ to Gly$^{32}$ and Pro$^{31}$ to Arg$^{33}$, were detected. These data raised the possibility that two independent turn-like conformational preferences occurred in this region of V3. The fact that a Pro$^{31}$-Arg$^{33}$ daN(i,i+2) NOE was unambiguously absent in C4-V3RF, and that a daN(i,I+2) NOE between Gly$^{30}$ and Gly$^{32}$ was also unambiguously absent in C4$_{E9G}$-V3RF(A), in spite of sequence identity in all three peptides, may be related to the weak intensity of these NOEs. Being close to the level of noise intensity, there is a possibility that one or both NOE signals on either side of the spectrum will not be detected, thus disallowing the given NOE to be scored as such.

Another region in V3 where conformational preferences could be inferred from NOEs occurs in residues Val$^{34}$-Ile$^{35}$-Tyr$^{36}$. In all three peptides NOEs were observed between the upfield methyl resonance (~0.67 ppm) of Val$^{34}$ and the ring hydrogens, both dH and eH, of Tyr$^{36}$. Weaker NOEs are also seen between the downfield methyl resonance (~0.89 ppm) of Val$^{34}$ and the ring hydrogens of Tyr$^{36}$. Further evidence of close proximity between the side-chains of Val$^{34}$ and Tyr$^{36}$ was the fact that the two methyl resonances of the former had disparate chemical shifts, compared to Val$^{10}$, consistent with a ring-current shift induced by the aromatic side-chain of Tyr. One peptide, C4-V3RF(A) had another NOE in this region, daN(i,i+2) between Ile$^{35}$ and Ala$^{37}$, that was unambiguously absent in the C4$_{E9G}$-V3RF(A) and C4$_{E9V}$-V3RF(A) peptides. This observation likely represented a poorly populated conformation, perhaps related to that which gives rise to the Val$^{34}$-Tyr$^{36}$ side-chain interaction, or from an independent conformational propensity.

Substitution of Lys$^{12}$ with Glu yielded a poorly immunogenic peptide (C4$_{K12E}$-V3RF(A)) that, interestingly had solution properties different from the other three peptides studied. Under the conditions used for NMR studies of other C4-V3 peptides, the solution of the C4$_{K12E}$-V3RF(A) peptides was highly viscous, and viscosity increased with pH in the vicinity of pH 4, implicating ionization of the Glu$^{12}$ side-chain in this phenomenon. NMR spectra of K12E at 278 K in aqueous buffer showed a much lower signal-to-noise ratio than the other three peptides. Increasing the temperature to 318 K or decreasing the pH to 3.5 yielded improved but still inadequate signal. Suitably high signal for resonance assignment and NOE analysis was obtained at 318 K, pH 3.5, 20% v/v trifluoroethanol (d$_3$). Even under this condition the NOEs for the C4$_{K12E}$-V3RF(A) were less intense than for other peptides.

Figure 2:
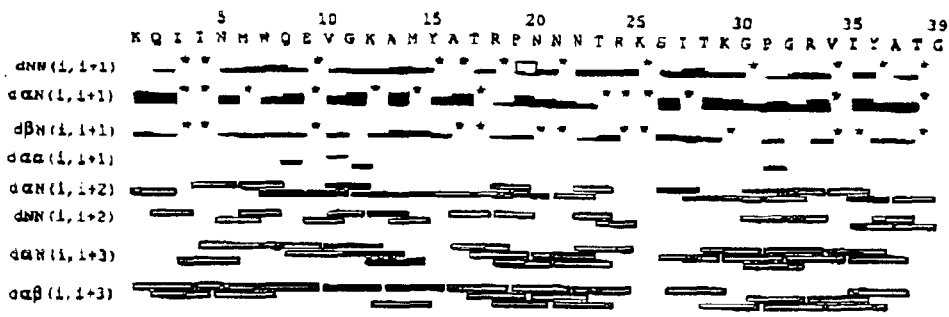
FIG. 2: NMR spectra of the four C4-V3RF valiant peptides (SEQ ID NOS 61–64, respectively, in order of appearance).
Figure 2:
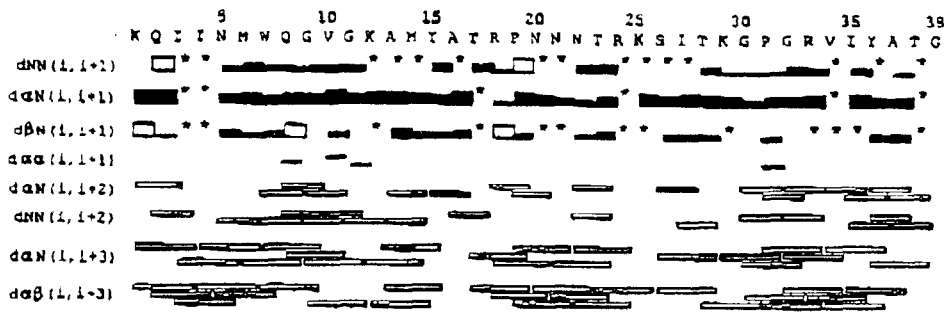
Figure 2:
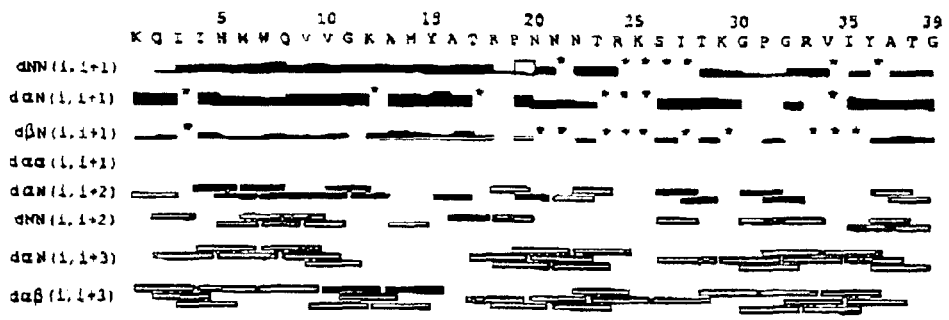
Figure 2:
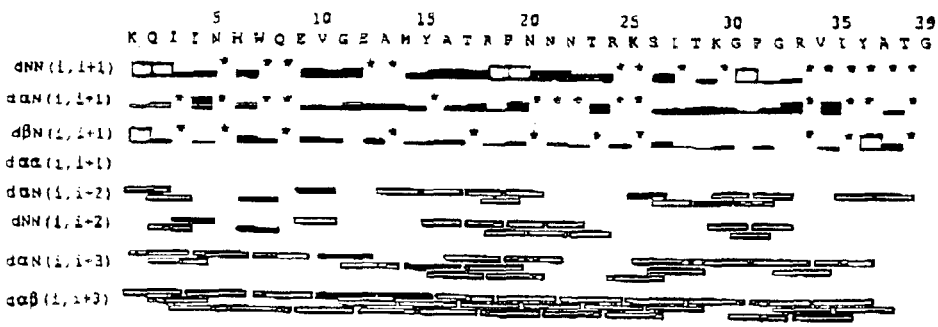

NOE connectivities in the C4 segment of C4$_{K12E}$-V3RF (A) (FIG. 2) show evidence of nascent helical turns in the region between Ile$^3$ and Gly$^{11}$ as inferred from dNN(i, i+2) and daN(i,i+2) NOEs. The stretch from Val$^{10}$ to Thr$^{17}$ has two daN(i,i+3) and two dab(i,i+3) NOEs suggesting the presence of a significant population with full helical turns. Within the V3 segment only two medium range NOEs are observed, both daN(i,i+2). Neither corresponds to NOEs observed in the other three peptides, but both NOEs involve residues of the Ser$^{26}$-Ile$^{27}$-Thr$^{28}$ sequence, for which there is evidence of conformational preferences in the other three peptides. A dbN(i,i+2) NOE between Ser$^{26}$ and Thr$^{28}$, observed in C4$_{E9V}$-V3RF(A)) and C4$_{E9G}$-V3RF(A), is also observed in the K12E peptide. Also observed are NOEs between the side-chains of Val$^{34}$ and Tyr$^{36}$. Hence the conformations giving rise to these two features are at least partially preserved under the solution conditions employed for K12E. Differences in the V3 segment between K12E and all of the other three peptides include the absence of detectable daN(i, 1+2) NOE between Pro$^{19}$ and Asn$^{21}$ and between Ser$^{26}$ and Thr$^{28}$. The failure to detect these NOEs may be due to the overall weaker signals of this sample, or to depopulation of the relevant conformations by the solution conditions.

EXAMPLE 2

The peptides in Table 7 have been studied in groups of 5 peptides as indicated in Table 9 (SEQ ID NOS 35, 49–51, 60, 42, 44, 48, 55, 57, 39, 43, 45, 53, 56, 33, 41, 46, 52, 58, 32, 40, 47, 54, 59, 31, 34 and 36–38, respectively, in order of appearance) and each group of 5 peptides has been injected into each of three guinea pigs in Freund's complete then incomplete adjuvant. After 4 immunizations, the animals were bled, and heat inactivated serum was pooled from each animal or tested separately as indicated in Table 8, for the ability to neutralize HIV. Single numbers per group indicate that the results are those of pooled sera from the group. Individual results per animal indicate that each serum was tested individually. Table 8 shows that all the sera neutralized to varying degrees the T cell line adapted HIV isolate MN and poorly neutralized the TCLA HIV isolate IIIB. Regarding the rest of the isolates in Table 8, all of which are HIV primary isolates (89.6, BAL ADA, SF162, 5768, QH0515, PVO, JRFL, BX08, 6101, SS1196), Group C sera from C4-V3 subtype B peptides neutralized 4/11 (36%) and Group F sera from subtype B peptides neutralized 5/11 primary isolates (45%). FIG. 4 shows that for the HIV CCR5 utilizing primary isolate, BAL, that the individual peptides in the 5-valent mixture absorbed out the neutralizing activity against HIV BAL to varying degrees, whereas the mixture of all the peptides completely absorbed out the neutralizing activity.

TABLE 8

Neutralization Of HIV-1 Isolates By Sera From Guinea Pigs Immunized With C4-V3 Clade B Peptides

| Animal | Immunogen | HIVMN# | HIVIIIB# | SHIV89.6# | SHIV89.6# | HIVBAL* |
|---|---|---|---|---|---|---|
| 477 | A | 2,258 | 0 | 96 | | 0 |
| 478 | A | 1,357 | 0 | NA | 35 | 0 |
| 479 | A | 4,632 | 68 | NA | | 0 |
| 480 | B | 1358 | 0 | NA | | 0 |
| 481 | B | 7,774 | 0 | NA | 27 | 84 |
| 482 | B | 4,241 | 0 | 62 | | 0 |
| 483 | C | 969 | 0 | 112 | | 95 |
| 484 | C | 806 | 0 | 20 | 97 | 84 |

TABLE 8-continued

Neutralization Of HIV-1 Isolates By Sera From Guinea Pigs Immunized With C4-V3 Clade B Peptides

| | | | | | | | |
|---|---|---|---|---|---|---|---|
| 485 | C | 542 | 0 | 226 | | | 80 |
| 486 | D | 1,488 | 0 | NA | | | 0 |
| 487 | D | 2,184 | 0 | NA | | 98 | 80 |
| 488 | D | 575 | 0 | NA | | | 0 |
| 489 | E | 3,223 | 0 | NA | | | 88 |
| 490 | E | NA | 0 | NA | | 255 | 0 |
| 491 | E | 519 | 0 | NA | | | 81 |
| 492 | F | NA | 0 | NA | | | NA |
| 493 | F | 910 | 0 | NA | | 0 | 91 |
| 494 | F | 1,159 | 35 | NA | | | NA |

| Animal | ADA* | SF162* | 5768* | QH0515* | PV0* | JRFL* | BXD8* | 6101* | SS1196* |
|---|---|---|---|---|---|---|---|---|---|
| 477 | | | | | | | | | |
| 478 | 0 | 90 | 0 | 0 | 0 | 0 | 0 | 0 | 85 |
| 479 | | | | | | | | | |
| 480 | | | | | | | | | |
| 481 | 0 | 96 | 0 | 0 | 0 | 0 | 0 | 0 | 0 |
| 482 | | | | | | | | | |
| 483 | | | | | | | | | |
| 484 | 0 | 99 | 0 | 0 | 0 | 0 | 86 | 0 | 0 |
| 485 | | | | | | | | | |
| 486 | | | | | | | | | |
| 487 | 0 | 98 | 0 | 0 | 0 | 0 | 94 | 0 | 0 |
| 488 | | | | | | | | | |
| 489 | | | | | | | | | |
| 490 | 0 | 92 | 0 | 0 | 0 | 0 | 0 | 0 | 0 |
| 491 | | | | | | | | | |
| 492 | | | | | | | | | |
| 493 | 0 | 84 | 0 | 0 | 0 | 0 | 91 | 94 | 88 |
| 494 | | | | | | | | | |

Assay titers are reciprocal serum dilutions at which 50% of MT-2 cells were protected from virus-induced killing as measured by neutral red uptake.
*% reduction in p24 synthesis relative to the amount of p24 synthesized in the presence of corresponding prebleed samples
Values >80% are positive.
NA = Not available.

TABLE 9

G. Pig Immunization Protocol Part 2

Immunization with a group of 5 peptides

| Peptide Name | Peptide Sequence | Code | GP No. |
|---|---|---|---|
| C4-V3 peptide | | | |
| C4-V3-23.38 | KQIINMWQVVGKAMYA-RPIKIERKRIPLGLGKAFYTTK | A | 477, 478, 479 |
| C4-V3-11.85 | KQIINMWQVVGKAMYA-RPNNNTRKSINIGPGRAFYTTG | A | |
| C4-V3-34.29 | KQIINMWQVVGKAMYA-RPNNNTRKSIQIGPGRAFYTTG | A | |
| C4-V3-1.481 | KQIINMWQVVGKAMYA-RPNNNTRKSIHIGPGRAFYTTG | A | |
| C4-V3-3.323 | KQIINMWQVVGKAMYA-RPNNNTRKSINMGPGRAFYTTG | A | |
| C4-V3-51.23 | KQIINMWQVVGKAMYA-RPSNNTRRSIHMGLGRAFYTTG | B | 480, 481, 482 |
| C4-V3-36.29 | KQIINMWQVVGKAMYA-RPNNNTRKGIHIGPGRTFFATG | B | |
| C4-V3-57.20 | KQIINMWQVVGKAMYA-RPNRHTGKSIRMGLGRAWHTTR | B | |
| C4-V3-35.29 | KQIINMWQVVGKAMYA-RPNNNTRKRISLGPGRVYYTTG | B | |
| C4-V3-46.26 | KQIINMWQVVGKAMYA-RPDNTIKQRIIHIGPGRPFYTT | B | |
| C4-V3-69.18 | KQIINMWQVVGKAMYA-RPNNNTRKSIRIGPGRAVYATD | C | 483, 484, 485 |
| C4-V3-72.18 | KQIINMWQVVGKAMYA-RPNNNTRKGINIGPGRAFYATG | C | |
| C4-V3-70.18 | KQIINMWQVVGKAMYA-RPNNNTRKRIRIGHIGPGRAFYATG | C | |
| C4-V3-62.19 | KQIINMWQVVGKAMYA-RPNNNTRKSIHIGPGRAFYATE | C | |
| C4-V3-74.17 | KQIINMWQVVGKAMYA-RPNNNTRKRMTLGPGKVFYTTG | C | |
| C4-V3-82.15 | KQIINMWQVVGKAMYA-RPNNNTRRSIPIGPGRAFYTTG | D | 486, 487, 487 |
| C4-V3-113.1 | KQIINMWQVVGKAMYA-RPNNNTRRSIHLGMGRALYATG | D | |
| C4-V3-89.14 | KQIINMWQVVGKAMYA-RPSINKRRHIHIGPGRAFYAT | D | |
| C4-V3-85.15 | KQIINMWQVVGKAMYA-RPNNNTRKSIHIAPGRAFYTTG | D | |
| C4-V3-122.9 | KQIINMWQVVGKAMYA-RPNYNETKRIRIHRGYGRSFVTVR | D | |
| C4-V3-170.6 | KQIINMWQVVGKAMYA-RPNNNTRRSVRIGPGGAMFRTG | E | 489, 490, 491 |
| C4-V3-146.8 | KQIINMWQVVGKAMYA-RPGNNTRRSISIGPGRAFVATK | E | |
| C4-V3-163.7 | KQIINMWQVVGKAMYA-RLYNYRRKGIHIGPGRAIYATG | E | |
| C4-V3-125.9 | KQIINMWQVVGKAMYA-RPNNNTRRRISMGPGRVLYTTG | E | |
| C4-V3-162.7 | KQIINMWQVVGKAMYA-RPGNNTRGSIHLHPGRKFYYSR | E | |
| C4-V3-396.2 | KQIINMWQVVGKAMYA-RPNNNTRRNIHIGLGRRFYAT | F | 492, 493, 494 |

TABLE 9-continued

G. Pig Immunization Protocol Part 2

| Peptide Name | Immunization with a group of 5 peptides<br>Peptide Sequence | Code | GP No. |
|---|---|---|---|
| C4-V3-144.8 | KQIINMWQVVGKAMYA-RPDNNTVRKIPIGPGSSFYTT | F | |
| C4-V3-365.2 | KQIINMWQVVGKAMYA-RPSNNTRKGIHLGPGRAIYATE | F | |
| C4-V3-513.2 | KQIINMWQVVGKAMYA-RPSNNTRKGIHMGPGKAIYTTD | F | |
| C4-V3-1448.1 | KQIINMWQVVGKAMYA-RPGNTTRRGIPIGPGRAFFTTG | F | |

It is important to be able to use T helper determinants with the V3 portion of the peptides shown in Table 7, both to expand the T helper activity in the immunogen, and in case any of the T helper peptides should be found to have any deleterious effects in the course of human trials. For example, it has recently been found in vitro that in culture of HIV and T cells, that the C4 portion of the C4-V3 peptide can augment HIV induced syncytium formation. However, peptides of this general design have been studied in vitro in HIV-infected humans (AIDS 12:1291–1300, 1998) and no subjects developed a ≧10 fold change in plasma HIV RNA levels from baseline. Moreover, the primary use of these peptides is as an immunogen in HIV-subjects as a preventive vaccine, and not in doses that one would consider for therapy, which would be in milligram amounts daily. A T helper determinant from HIV gag, termed GTH1 with the sequence of Y K R W I I L G L N K I V R M Y S (SEQ ID NO:5) has been conjugated to the V3 of HIV MN and found to induce anti-HIV MN titers of 1:3200. Similarly, GTH1 conjugated to a V3 sequence of a HIV primary isolate DU179 induced antibodies that neutralized HIV MN (1:192) and neutralized the HIV primary isolate JR-FL (90% p24 reduction in PBMC cultures). Thus, the GTH1 T helper sequence can substitute for the C4 sequence in the peptides in Table 7.

Finally, a panel of monovalent serum from individual guinea pigs immunized with each of the peptides in Table 7 has been screened. Whereas most of the peptides in the list only induced neutralizing antibodies that neutralized 0 to 6 out of 19 primary isolates, 5 peptides were found that neutralized from 14 to 19 out of 19 primary isolates tested. These peptides were C4-V3 36.29, C4-V3 34.29, C4-V3 62.19, C4-V3 74.17, and C4-V3 162.7. The sequences of these peptides are all listed in Table 7.

Thus, sufficient breadth has been observed both in mixtures of C4-V3 peptides and in select individual peptides for the immunogen to be practical with regard to induction of neutralizing antibodies against HIV primary isolates. By performing the same immunization studies with the similarly designed HIV subtype (clade) C peptides in Table 6, that a similar immunogen(s) can be developed for HIV subtype C viruses.

While individual peptides can be used to achieve the breadth of neutralizing activity needed to protect against HIV primary isolates, advantageously, mixtures of multiple peptides are used, such as the combination of group C, or group F or the combination of C4-V3 36.29, C4-V3 34.29, C4-V3 62.19, C4-V3 74.17, and C4-V3 162.7 peptides described above.

All documents cited above are hereby incorporated in their entirety by reference.

What is claimed is:

1. A composition comprising a multiplicity of immunogenic peptides comprising a first and a second component,
    said first component comprising residues of the C4 domain of HIV gp120 and including a T-helper epitope,
    said second component comprising residues of the V3 domain of gp120 and including a B cell neutralizing antibody epitope,
    wherein at least one of said peptides comprises the sequence of SEQ ID NO:53.

2. The composition according to claim 1 wherein said first component of each of said peptides comprises at least 16 contiguous residues of the C4 domain of HIV gp120.

3. The composition according to claim 2 wherein said first component of each of said peptides comprises residues 421 to 436 of HIV gp120.

4. The composition according to claim 1 wherein said first component of each of said peptides comprises at least 16 contiguous residues of the C4 domain of HIV gp120 and said second component of each of said peptides comprises at least 23 contiguous residues of the V3 domain of HIV gp120.

5. The composition according to claim 4 wherein said first component comprises residues 421 to 436 of HIV gp120 and said second component comprises residues 297 to 322 of HIV gp120.

6. The composition according to claim 1 wherein said second component is linked C terminal to said first component.

7. The composition according to claim 1 wherein said first component is linked to said second component via a linker.

8. The composition according to claim 1 wherein said composition comprises at least 5 different immunogenic peptides.

9. The composition according to claim 8, wherein said composition comprises C4-V3 36.29 (SEQ ID NO:44), C4-V3 34.29 (SEQ ID NO:50), C4-V3 74.17 (SEQ ID NO:56) and C4-V3 162.7 (SEQ ID NO: 59) from Table 7.

10. The composition according to claim 8 wherein said composition comprises at least 10 different immunogenic peptides.

11. The composition according to claim 10 wherein said composition comprises at least 25 different immunogenic peptides.

12. The composition according to claim 1 wherein said composition further comprises a carrier.

13. The composition according to claim 1 wherein said composition further comprises an adjuvant.

14. A method of inducing the production of antibodies in a patient comprising administering to said patient an amount of the composition according to claim 1 sufficient to effect said production.

15. A composition comprising the peptide of SEQ ID NO:53 and a carrier.

16. The composition according to claim 15 wherein said composition further comprises an adjuvant.

* * * * *

UNITED STATES PATENT AND TRADEMARK OFFICE
CERTIFICATE OF CORRECTION

| | | |
|---|---|---|
| PATENT NO. | : 7,153,509 B2 | Page 1 of 1 |
| APPLICATION NO. | : 10/289228 | |
| DATED | : December 26, 2006 | |
| INVENTOR(S) | : Haynes et al. | |

It is certified that error appears in the above-identified patent and that said Letters Patent is hereby corrected as shown below:

Column 1, line 8, before the heading entitled "TECHNICAL FIELD" insert the following new paragraph:

This invention was made with Government support under Contract No. DE-AC52-06NA25396 awarded by the U.S. Department of Energy. The Government has certain rights in the invention.

Signed and Sealed this

Twenty-ninth Day of May, 2007

JON W. DUDAS
*Director of the United States Patent and Trademark Office*

SEQUENCE LISTING

```
<160> NUMBER OF SEQ ID NOS: 65

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 1

Lys Gln Ile Ile Asn Met Trp Gln Glu Val Gly Lys Ala Met Tyr Ala
 1               5                  10                  15

Thr Arg Pro Asn Asn Asn Thr Arg Arg Arg Leu Ser Ile Gly Pro Gly
            20                  25                  30

Arg Ala Phe Tyr Ala Arg Arg
        35

<210> SEQ ID NO 2
<211> LENGTH: 39
<212> TYPE: PRT
<213> ORGANISM: Artificial Sequence
```

-continued

```
<220> FEATURE:
<223> OTHER INFORMATION: Description of Artificial Sequence:Human
      Immunodeficiency Virus

<400> SEQUENCE: 2

Lys Gln Ile Ile Asn Met Trp Gln Val Val Gly Lys Ala Met Tyr Ala
 1               5                  10                  15

Thr Arg Pro Asn Asn Asn Thr Arg Arg Arg Leu Ser Ile Gly Pro Gly
            20                  25                  30

Arg Ala Phe Tyr Ala Arg Arg
        35

<210> SEQ ID NO 3
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 3

Lys Gln Ile Ile Asn Met Trp Gln Glu Val Gly Lys Ala Met Tyr Ala
 1               5                  10                  15

Thr Arg Pro Asn Asn Asn Thr Arg Glu Arg Leu Ser Ile Gly Pro Gly
            20                  25                  30

Arg Ala Phe Tyr Ala Arg Arg
        35

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 4

Lys Gln Ile Ile Asn Met Trp Gln Val Val Gly Lys Ala Met Tyr Ala
 1               5                  10                  15

Thr Arg Pro Asn Asn Asn Thr Arg Glu Arg Leu Ser Ile Gly Pro Gly
            20                  25                  30

Arg Ala Phe Tyr Ala Arg Arg
        35

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 5

Tyr Lys Arg Trp Ile Ile Leu Gly Leu Asn Lys Ile Val Arg Met Tyr
 1               5                  10                  15

Ser

<210> SEQ ID NO 6
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus
```

```
<400> SEQUENCE: 6

Lys Gln Ile Ile Asn Met Trp Gln Val Val Gly Lys Ala Met Tyr Ala
  1               5                  10                  15

Thr Arg Pro Asn Asn Asn Thr Arg Lys Ser Ile Arg Ile Gly Pro Gly
             20                  25                  30

Gln Thr Phe Tyr Ala Thr Gly
         35

<210> SEQ ID NO 7
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 7

Lys Gln Ile Ile Asn Met Trp Gln Val Val Gly Lys Ala Met Tyr Ala
  1               5                  10                  15

Thr Arg Pro Asn Asn Asn Thr Arg Lys Ser Ile Arg Ile Gly Pro Gly
             20                  25                  30

Gln Thr Phe Tyr Ala Arg Gly
         35

<210> SEQ ID NO 8
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 8

Lys Gln Ile Ile Asn Met Trp Gln Val Val Gly Lys Ala Met Tyr Ala
  1               5                  10                  15

Thr Arg Pro Asn Asn Asn Thr Arg Lys Ser Ile Arg Ile Gly Pro Gly
             20                  25                  30

Gln Thr Phe Tyr Ala Ala Gly
         35

<210> SEQ ID NO 9
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 9

Lys Gln Ile Ile Asn Met Trp Gln Val Val Gly Lys Ala Met Tyr Ala
  1               5                  10                  15

Ile Arg Pro Asn Asn Asn Thr Arg Lys Ser Val Arg Ile Gly Pro Gly
             20                  25                  30

Gln Thr Phe Tyr Ala Thr Gly
         35

<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence:Human
```

```
Immunodeficiency Virus

<400> SEQUENCE: 10

Lys Gln Ile Ile Asn Met Trp Gln Val Val Gly Lys Ala Met Tyr Ala
 1               5                  10                  15

Thr Arg Pro Asn Asn Thr Arg Lys Ser Ile Arg Ile Gly Pro Gly
            20                  25                  30

Gln Thr Phe Phe Ala Thr Gly
        35

<210> SEQ ID NO 11
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 11

Lys Gln Ile Ile Asn Met Trp Gln Val Val Gly Lys Ala Met Tyr Ala
 1               5                  10                  15

Thr Arg Pro Asn Asn Thr Arg Lys Ser Ile Arg Ile Gly Pro Gly
            20                  25                  30

Gln Thr Phe Tyr Ala Thr Asn
        35

<210> SEQ ID NO 12
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 12

Lys Gln Ile Ile Asn Met Trp Gln Val Val Gly Lys Ala Met Tyr Ala
 1               5                  10                  15

Thr Arg Pro Asn Asn Thr Arg Glu Ser Ile Arg Ile Gly Pro Gly
            20                  25                  30

Gln Thr Phe Tyr Ala Thr Gly
        35

<210> SEQ ID NO 13
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 13

Lys Gln Ile Ile Asn Met Trp Gln Val Val Gly Lys Ala Met Tyr Ala
 1               5                  10                  15

Thr Arg Pro Asn Asn Thr Arg Arg Ser Ile Arg Ile Gly Pro Gly
            20                  25                  30

Gln Ala Phe Tyr Ala Thr Gly
        35

<210> SEQ ID NO 14
<211> LENGTH: 39
<212> TYPE: PRT
<213> ORGANISM: Artificial Sequence
<220> FEATURE:
```

<223> OTHER INFORMATION: Description of Artificial Sequence:Human
      Immunodeficiency Virus

<400> SEQUENCE: 14

Lys Gln Ile Ile Asn Met Trp Gln Val Val Gly Lys Ala Met Tyr Ala
 1               5                  10                  15

Thr Arg Pro Asn Asn Asn Thr Arg Lys Gly Ile Arg Ile Gly Pro Gly
            20                  25                  30

Gln Thr Phe Tyr Ala Thr Gly
        35

<210> SEQ ID NO 15
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 15

Lys Gln Ile Ile Asn Met Trp Gln Val Val Gly Lys Ala Met Tyr Ala
 1               5                  10                  15

Thr Arg Pro Ser Asn Asn Thr Arg Lys Ser Ile Arg Ile Gly Pro Gly
            20                  25                  30

Gln Ala Phe Tyr Ala Thr Gly
        35

<210> SEQ ID NO 16
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 16

Lys Gln Ile Ile Asn Met Trp Gln Val Val Gly Lys Ala Met Tyr Ala
 1               5                  10                  15

Thr Arg Pro Ser Asn Asn Thr Arg Lys Ser Ile Arg Ile Gly Pro Gly
            20                  25                  30

Gln Thr Phe Tyr Ala Thr Asn
        35

<210> SEQ ID NO 17
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 17

Lys Gln Ile Ile Asn Met Trp Gln Val Val Gly Lys Ala Met Tyr Ala
 1               5                  10                  15

Thr Arg Pro Ser Asn Asn Thr Arg Glu Ser Ile Arg Ile Gly Pro Gly
            20                  25                  30

Gln Thr Phe Tyr Ala Thr Gly
        35

<210> SEQ ID NO 18
<211> LENGTH: 39
<212> TYPE: PRT
<213> ORGANISM: Artificial Sequence

```
<220> FEATURE:
<223> OTHER INFORMATION: Description of Artificial Sequence:Human
      Immunodeficiency Virus

<400> SEQUENCE: 18

Lys Gln Ile Ile Asn Met Trp Gln Val Val Gly Lys Ala Met Tyr Ala
 1               5                  10                  15

Thr Arg Pro Asn Asn Asn Thr Arg Lys Ser Met Arg Ile Gly Pro Gly
            20                  25                  30

Gln Thr Phe Tyr Ala Thr Gly
        35

<210> SEQ ID NO 19
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 19

Lys Gln Ile Ile Asn Met Trp Gln Val Val Gly Lys Ala Met Tyr Ala
 1               5                  10                  15

Thr Arg Pro Gly Asn Asn Thr Arg Lys Ser Met Arg Ile Gly Pro Gly
            20                  25                  30

Gln Thr Phe Tyr Ala Thr Gly
        35

<210> SEQ ID NO 20
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 20

Lys Gln Ile Ile Asn Met Trp Gln Val Val Gly Lys Ala Met Tyr Ala
 1               5                  10                  15

Thr Arg Pro Gly Asn Asn Thr Arg Lys Ser Ile Arg Ile Gly Pro Gly
            20                  25                  30

Gln Thr Leu Tyr Ala Thr Gly
        35

<210> SEQ ID NO 21
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 21

Lys Gln Ile Ile Asn Met Trp Gln Val Val Gly Lys Ala Met Tyr Ala
 1               5                  10                  15

Val Arg Pro Asn Asn Asn Thr Arg Lys Ser Val Arg Ile Gly Pro Gly
            20                  25                  30

Gln Thr Ser Tyr Ala Thr Gly
        35

<210> SEQ ID NO 22
<211> LENGTH: 39
<212> TYPE: PRT
```

```
<213> ORGANISM: Artificial Sequence
<220> FEATURE:
<223> OTHER INFORMATION: Description of Artificial Sequence:Human
      Immunodeficiency Virus

<400> SEQUENCE: 22

Lys Gln Ile Ile Asn Met Trp Gln Val Val Gly Lys Ala Met Tyr Ala
 1               5                  10                  15

Thr Arg Pro Gly Asn Asn Thr Arg Arg Ser Ile Arg Ile Gly Pro Gly
             20                  25                  30

Gln Thr Phe Tyr Ala Thr Gly
         35

<210> SEQ ID NO 23
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 23

Lys Gln Ile Ile Asn Met Trp Gln Val Val Gly Lys Ala Met Tyr Ala
 1               5                  10                  15

Ile Arg Pro Gly Asn Asn Thr Arg Lys Ser Val Arg Ile Gly Pro Gly
             20                  25                  30

Gln Thr Phe Tyr Ala Thr Gly
         35

<210> SEQ ID NO 24
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 24

Lys Gln Ile Ile Asn Met Trp Gln Val Val Gly Lys Ala Met Tyr Ala
 1               5                  10                  15

Thr Arg Pro Asn Asn Asn Thr Arg Lys Ser Ile Arg Ile Gly Pro Gly
             20                  25                  30

Gln Ala Phe Tyr Ala Thr Asn
         35

<210> SEQ ID NO 25
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 25

Lys Gln Ile Ile Asn Met Trp Gln Val Val Gly Lys Ala Met Tyr Ala
 1               5                  10                  15

Thr Arg Pro Asn Asn Asn Thr Arg Gln Ser Ile Arg Ile Gly Pro Gly
             20                  25                  30

Gln Ala Phe Tyr Ala Thr Lys
         35

<210> SEQ ID NO 26
<211> LENGTH: 39
```

```
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 26

Lys Gln Ile Ile Asn Met Trp Gln Val Val Gly Lys Ala Met Tyr Ala
  1               5                  10                  15

Thr Arg Pro Gly Asn Asn Thr Arg Lys Ser Ile Arg Ile Gly Pro Gly
             20                  25                  30

Gln Ala Phe Phe Ala Thr Gly
         35

<210> SEQ ID NO 27
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 27

Lys Gln Ile Ile Asn Met Trp Gln Val Val Gly Lys Ala Met Tyr Ala
  1               5                  10                  15

Thr Arg Pro Gly Asn Asn Thr Arg Lys Ser Val Arg Ile Gly Pro Gly
             20                  25                  30

Gln Ala Phe Tyr Ala Thr Asn
         35

<210> SEQ ID NO 28
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 28

Lys Gln Ile Ile Asn Met Trp Gln Val Val Gly Lys Ala Met Tyr Ala
  1               5                  10                  15

Thr Arg Pro Asn Asn Asn Thr Arg Lys Gly Ile His Ile Gly Pro Gly
             20                  25                  30

Gln Ala Phe Tyr Ala Ala Gly
         35

<210> SEQ ID NO 29
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 29

Lys Gln Ile Ile Asn Met Trp Gln Val Val Gly Lys Ala Met Tyr Ala
  1               5                  10                  15

Thr Arg Pro Asn Asn Asn Thr Arg Lys Gly Ile Gly Ile Gly Pro Gly
             20                  25                  30

Gln Thr Phe Phe Ala Thr Glu
         35

<210> SEQ ID NO 30
```

-continued

```
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 30

Lys Gln Ile Ile Asn Met Trp Gln Val Val Gly Lys Ala Met Tyr Ala
  1               5                  10                  15

Thr Arg Pro Gly Asn Asn Thr Arg Glu Ser Ile Gly Ile Gly Pro Gly
             20                  25                  30

Gln Ala Phe Tyr Ala Thr Gly
         35

<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 31

Lys Gln Ile Ile Asn Met Trp Gln Val Val Gly Lys Ala Met Tyr Ala
  1               5                  10                  15

Arg Pro Asn Asn Thr Arg Arg Asn Ile His Ile Gly Leu Gly Arg
             20                  25                  30

Arg Phe Tyr Ala Thr
         35

<210> SEQ ID NO 32
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 32

Lys Gln Ile Ile Asn Met Trp Gln Val Val Gly Lys Ala Met Tyr Ala
  1               5                  10                  15

Arg Pro Asn Asn Asn Thr Arg Arg Ser Val Arg Ile Gly Pro Gly Gly
             20                  25                  30

Ala Met Phe Arg Thr Gly
         35

<210> SEQ ID NO 33
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 33

Lys Gln Ile Ile Asn Met Trp Gln Val Val Gly Lys Ala Met Tyr Ala
  1               5                  10                  15

Arg Pro Asn Asn Asn Thr Arg Arg Ser Ile Pro Ile Gly Pro Gly Arg
             20                  25                  30

Ala Phe Tyr Thr Thr Gly
         35
```

```
<210> SEQ ID NO 34
<211> LENGTH: 37
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 34

Lys Gln Ile Ile Asn Met Trp Gln Val Val Gly Lys Ala Met Tyr Ala
 1               5                  10                  15

Arg Pro Asp Asn Asn Thr Val Arg Lys Ile Pro Ile Gly Pro Gly Ser
            20                  25                  30

Ser Phe Tyr Thr Thr
        35

<210> SEQ ID NO 35
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 35

Lys Gln Ile Ile Asn Met Trp Gln Val Val Gly Lys Ala Met Tyr Ala
 1               5                  10                  15

Arg Pro Ile Lys Ile Glu Arg Lys Arg Ile Pro Leu Gly Leu Gly Lys
            20                  25                  30

Ala Phe Tyr Thr Thr Lys
        35

<210> SEQ ID NO 36
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 36

Lys Gln Ile Ile Asn Met Trp Gln Val Val Gly Lys Ala Met Tyr Ala
 1               5                  10                  15

Arg Pro Ser Asn Asn Thr Arg Lys Gly Ile His Leu Gly Pro Gly Arg
            20                  25                  30

Ala Ile Tyr Ala Thr Glu
        35

<210> SEQ ID NO 37
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 37

Lys Gln Ile Ile Asn Met Trp Gln Val Val Gly Lys Ala Met Tyr Ala
 1               5                  10                  15

Arg Pro Ser Asn Asn Thr Arg Lys Gly Ile His Met Gly Pro Gly Lys
            20                  25                  30

Ala Ile Tyr Thr Thr Asp
        35
```

```
<210> SEQ ID NO 38
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 38

Lys Gln Ile Ile Asn Met Trp Gln Val Val Gly Lys Ala Met Tyr Ala
  1               5                  10                  15

Arg Pro Gly Asn Thr Thr Arg Arg Gly Ile Pro Ile Gly Pro Gly Arg
             20                  25                  30

Ala Phe Phe Thr Thr Gly
             35

<210> SEQ ID NO 39
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 39

Lys Gln Ile Ile Asn Met Trp Gln Val Val Gly Lys Ala Met Tyr Ala
  1               5                  10                  15

Arg Pro Asn Asn Asn Thr Arg Lys Ser Ile Arg Ile Gly Pro Gly Arg
             20                  25                  30

Ala Val Tyr Ala Thr Asp
             35

<210> SEQ ID NO 40
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 40

Lys Gln Ile Ile Asn Met Trp Gln Val Val Gly Lys Ala Met Tyr Ala
  1               5                  10                  15

Arg Pro Gly Asn Asn Thr Arg Arg Arg Ile Ser Ile Gly Pro Gly Arg
             20                  25                  30

Ala Phe Val Ala Thr Lys
             35

<210> SEQ ID NO 41
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 41

Lys Gln Ile Ile Asn Met Trp Gln Val Val Gly Lys Ala Met Tyr Ala
  1               5                  10                  15

Arg Pro Asn Asn Asn Thr Arg Arg Ser Ile His Leu Gly Met Gly Arg
             20                  25                  30

Ala Leu Tyr Ala Thr Gly
             35
```

```
<210> SEQ ID NO 42
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 42

Lys Gln Ile Ile Asn Met Trp Gln Val Val Gly Lys Ala Met Tyr Ala
 1               5                  10                  15

Arg Pro Ser Asn Asn Thr Arg Arg Ser Ile His Met Gly Leu Gly Arg
            20                  25                  30

Ala Phe Tyr Thr Thr Gly
        35

<210> SEQ ID NO 43
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 43

Lys Gln Ile Ile Asn Met Trp Gln Val Val Gly Lys Ala Met Tyr Ala
 1               5                  10                  15

Arg Pro Asn Asn Asn Thr Arg Lys Gly Ile Asn Ile Gly Pro Gly Arg
            20                  25                  30

Ala Phe Tyr Ala Thr Gly
        35

<210> SEQ ID NO 44
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 44

Lys Gln Ile Ile Asn Met Trp Gln Val Val Gly Lys Ala Met Tyr Ala
 1               5                  10                  15

Arg Pro Asn Asn Asn Thr Arg Lys Gly Ile His Ile Gly Pro Gly Arg
            20                  25                  30

Thr Phe Phe Ala Thr Gly
        35

<210> SEQ ID NO 45
<211> LENGTH: 41
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 45

Lys Gln Ile Ile Asn Met Trp Gln Val Val Gly Lys Ala Met Tyr Ala
 1               5                  10                  15

Arg Pro Asn Asn Asn Thr Arg Lys Arg Ile Arg Ile Gly His Ile Gly
            20                  25                  30

Pro Gly Arg Ala Phe Tyr Ala Thr Gly
```

```
                35                  40

<210> SEQ ID NO 46
<211> LENGTH: 37
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 46

Lys Gln Ile Ile Asn Met Trp Gln Val Val Gly Lys Ala Met Tyr Ala
  1               5                  10                  15

Arg Pro Ser Ile Asn Lys Arg Arg His Ile His Ile Gly Pro Gly Arg
             20                  25                  30

Ala Phe Tyr Ala Thr
             35

<210> SEQ ID NO 47
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 47

Lys Gln Ile Ile Asn Met Trp Gln Val Val Gly Lys Ala Met Tyr Ala
  1               5                  10                  15

Arg Leu Tyr Asn Tyr Arg Arg Lys Gly Ile His Ile Gly Pro Gly Arg
             20                  25                  30

Ala Ile Tyr Ala Thr Gly
             35

<210> SEQ ID NO 48
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 48

Lys Gln Ile Ile Asn Met Trp Gln Val Val Gly Lys Ala Met Tyr Ala
  1               5                  10                  15

Arg Pro Asn Arg His Thr Gly Lys Ser Ile Arg Met Gly Leu Gly Arg
             20                  25                  30

Ala Trp His Thr Thr Arg
             35

<210> SEQ ID NO 49
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 49

Lys Gln Ile Ile Asn Met Trp Gln Val Val Gly Lys Ala Met Tyr Ala
  1               5                  10                  15

Arg Pro Asn Asn Asn Thr Arg Lys Ser Ile Asn Ile Gly Pro Gly Arg
             20                  25                  30
```

Ala Phe Tyr Thr Thr Gly
        35

<210> SEQ ID NO 50
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 50

Lys Gln Ile Ile Asn Met Trp Gln Val Val Gly Lys Ala Met Tyr Ala
 1               5                  10                  15

Arg Pro Asn Asn Asn Thr Arg Lys Ser Ile Gln Ile Gly Pro Gly Arg
            20                  25                  30

Ala Phe Tyr Thr Thr Gly
        35

<210> SEQ ID NO 51
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 51

Lys Gln Ile Ile Asn Met Trp Gln Val Val Gly Lys Ala Met Tyr Ala
 1               5                  10                  15

Arg Pro Asn Asn Asn Thr Arg Lys Ser Ile His Ile Gly Pro Gly Arg
            20                  25                  30

Ala Phe Tyr Thr Thr Gly
        35

<210> SEQ ID NO 52
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 52

Lys Gln Ile Ile Asn Met Trp Gln Val Val Gly Lys Ala Met Tyr Ala
 1               5                  10                  15

Arg Pro Asn Asn Asn Thr Arg Lys Ser Ile His Ile Ala Pro Gly Arg
            20                  25                  30

Ala Phe Tyr Thr Thr Gly
        35

<210> SEQ ID NO 53
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 53

Lys Gln Ile Ile Asn Met Trp Gln Val Val Gly Lys Ala Met Tyr Ala
 1               5                  10                  15

Arg Pro Asn Asn Asn Thr Arg Lys Ser Ile His Ile Gly Pro Gly Arg
            20                  25                  30

Ala Phe Tyr Ala Thr Glu
        35

<210> SEQ ID NO 54
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 54

Lys Gln Ile Ile Asn Met Trp Gln Val Val Gly Lys Ala Met Tyr Ala
 1               5                  10                  15

Arg Pro Asn Asn Asn Thr Arg Arg Ile Ser Met Gly Pro Gly Arg
            20                  25                  30

Val Leu Tyr Thr Thr Gly
        35

<210> SEQ ID NO 55
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 55

Lys Gln Ile Ile Asn Met Trp Gln Val Val Gly Lys Ala Met Tyr Ala
 1               5                  10                  15

Arg Pro Asn Asn Asn Thr Arg Lys Arg Ile Ser Leu Gly Pro Gly Arg
            20                  25                  30

Val Tyr Tyr Thr Thr Gly
        35

<210> SEQ ID NO 56
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 56

Lys Gln Ile Ile Asn Met Trp Gln Val Val Gly Lys Ala Met Tyr Ala
 1               5                  10                  15

Arg Pro Asn Asn Asn Thr Arg Lys Arg Met Thr Leu Gly Pro Gly Lys
            20                  25                  30

Val Phe Tyr Thr Thr Gly
        35

<210> SEQ ID NO 57
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 57

Lys Gln Ile Ile Asn Met Trp Gln Val Val Gly Lys Ala Met Tyr Ala
 1               5                  10                  15

Arg Pro Asp Asn Thr Ile Lys Gln Arg Ile Ile His Ile Gly Pro Gly 20                  25                  30

Arg Pro Phe Tyr Thr Thr
            35

<210> SEQ ID NO 58
<211> LENGTH: 40
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 58

Lys Gln Ile Ile Asn Met Trp Gln Val Val Gly Lys Ala Met Tyr Ala
  1               5                  10                  15

Arg Pro Asn Tyr Asn Glu Thr Lys Arg Ile Arg Ile His Arg Gly Tyr
            20                  25                  30

Gly Arg Ser Phe Val Thr Val Arg
            35                  40

<210> SEQ ID NO 59
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 59

Lys Gln Ile Ile Asn Met Trp Gln Val Val Gly Lys Ala Met Tyr Ala
  1               5                  10                  15

Arg Pro Gly Asn Asn Thr Arg Gly Ser Ile His Leu His Pro Gly Arg
            20                  25                  30

Lys Phe Tyr Tyr Ser Arg
            35

<210> SEQ ID NO 60
<211> LENGTH: 38
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 60

Lys Gln Ile Ile Asn Met Trp Gln Val Val Gly Lys Ala Met Tyr Ala
  1               5                  10                  15

Arg Pro Asn Asn Asn Thr Arg Lys Ser Ile Asn Met Gly Pro Gly Arg
            20                  25                  30

Ala Phe Tyr Thr Thr Gly
            35

<210> SEQ ID NO 61
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 61

Lys Gln Ile Ile Asn Met Trp Gln Glu Val Gly Lys Ala Met Tyr Ala
  1               5                  10                  15

-continued

Thr Arg Pro Asn Asn Asn Thr Arg Lys Ser Ile Thr Lys Gly Pro Gly
            20                  25                  30

Arg Val Ile Tyr Ala Thr Gly
        35

<210> SEQ ID NO 62
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 62

Lys Gln Ile Ile Asn Met Trp Gln Gly Val Gly Lys Ala Met Tyr Ala
  1               5                  10                  15

Thr Arg Pro Asn Asn Asn Thr Arg Lys Ser Ile Thr Lys Gly Pro Gly
            20                  25                  30

Arg Val Ile Tyr Ala Thr Gly
        35

<210> SEQ ID NO 63
<211> LENGTH: 39
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 63

Lys Gln Ile Ile Asn Met Trp Gln Val Val Gly Lys Ala Met Tyr Ala
  1               5                  10                  15

Thr Arg Pro Asn Asn Asn Thr Arg Lys Ser Ile Thr Lys Gly Pro Gly
            20                  25                  30

Arg Val Ile Tyr Ala Thr Gly
        35

<210> SEQ ID NO 64
<211> LENGTH: 40
<212> TYPE: PRT
<213> ORGANISM: Artificial Sequence
<220> FEATURE:
<223> OTHER INFORMATION: Description of Artificial Sequence:Human
      Immunodeficiency Virus

<400> SEQUENCE: 64

Lys Gln Ile Ile Ile Asn Met Trp Gln Glu Val Gly Glu Ala Met Tyr
  1               5                  10                  15

Ala Thr Arg Pro Asn Asn Asn Thr Arg Lys Ser Ile Thr Lys Gly Pro
            20                  25                  30

Gly Arg Val Ile Tyr Ala Thr Gly
        35                  40

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence:Human
      Immunodeficiency Virus -continued

```
<400> SEQUENCE: 65

Lys Gln Ile Ile Asn Met Trp Gln Val Val Gly Lys Ala Met Tyr Ala
1               5                   10                  15
```